US012788384B2

(12) United States Patent
Fang

(10) Patent No.: US 12,788,384 B2
(45) Date of Patent: Nov. 10, 2026

(54) DEFECT OCCLUDER WITH WRAPPING COVER

(71) Applicant: EDWARDS LIFESCIENCES CORPORATION, Irvine, CA (US)

(72) Inventor: Diana Fang, Fullerton, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 77 days.

(21) Appl. No.: 18/585,926

(22) Filed: Feb. 23, 2024

(65) Prior Publication Data

US 2024/0188948 A1 Jun. 13, 2024

Related U.S. Application Data

(63) Continuation of application No. PCT/US2022/039336, filed on Aug. 3, 2022.

(60) Provisional application No. 63/237,475, filed on Aug. 26, 2021.

(51) Int. Cl.
*A61B 17/00* (2006.01)

(52) U.S. Cl.
CPC ............................... *A61B 17/0057* (2013.01); *A61B 2017/00575* (2013.01); *A61B 2017/00601* (2013.01)

(58) Field of Classification Search
CPC ........... A61B 2017/00606; A61B 2017/00597; A61B 2017/00592
See application file for complete search history.

(56) References Cited

U.S. PATENT DOCUMENTS

| | | | | |
|---|---|---|---|---|
| 5,702,421 | A * | 12/1997 | Schneidt ............ | A61B 17/1219 600/32 |
| 6,171,329 | B1 | 1/2001 | Shaw et al. | |
| 6,206,907 | B1 | 3/2001 | Marino et al. | |
| 6,706,064 | B1 * | 3/2004 | Anson .............. | A61B 17/12109 623/1.1 |
| 7,192,435 | B2 | 3/2007 | Corcoran et al. | |
| 7,582,104 | B2 | 9/2009 | Corcoran et al. | |
| 8,366,741 | B2 | 2/2013 | Chin et al. | |
| 8,372,113 | B2 | 2/2013 | Opolski | |
| 8,764,790 | B2 | 7/2014 | Thommen et al. | |

(Continued)

FOREIGN PATENT DOCUMENTS

| | | | |
|---|---|---|---|
| CN | 203677142 | U | 7/2014 |
| WO | 2016100866 | A1 | 6/2016 |
| WO | 2021058602 | A1 | 4/2021 |

OTHER PUBLICATIONS

Yong et al., "Device Closure for PFO" Cardiac Inventions Today Jun. 2007, pp. 32-40.

*Primary Examiner* — Alexander J Orkin
(74) *Attorney, Agent, or Firm* — Chang & Hale LLP

(57) ABSTRACT

An occluder device includes a core form having first and second axial ends, a first plurality of wires emanating radially from the first axial end of the core form, the first plurality of wires being configured to circumferentially wrap around an axis of the core form, a first covering coupled to at least one of the first plurality of wires or the first axial end of the core form, a second plurality of wires emanating radially from the second axial end of the core form, the second plurality of wires being configured to circumferentially wrap around the axis of the core form, and a second covering coupled to at least one of the second plurality of wires or the second axial end of the core form.

19 Claims, 19 Drawing Sheets

(56) References Cited

U.S. PATENT DOCUMENTS

| | | | | |
|---|---|---|---|---|
| 2004/0143291 | A1* | 7/2004 | Corcoran | A61B 17/0057 606/151 |
| 2006/0217761 | A1 | 9/2006 | Opolski | |
| 2007/0073337 | A1* | 3/2007 | Abbott | A61B 17/0057 606/213 |
| 2012/0010653 | A1* | 1/2012 | Seifert | A61B 17/0057 606/213 |
| 2012/0029556 | A1* | 2/2012 | Masters | A61B 17/0057 606/213 |
| 2012/0143242 | A1 | 6/2012 | Masters | |
| 2012/0150218 | A1* | 6/2012 | Sandgren | A61B 17/0057 606/213 |
| 2013/0110228 | A1 | 5/2013 | Braido | |
| 2014/0012368 | A1 | 1/2014 | Sugimoto et al. | |
| 2015/0005810 | A1* | 1/2015 | Center | A61F 2/01 606/200 |
| 2016/0262768 | A1 | 9/2016 | Haverkost et al. | |
| 2017/0367710 | A1 | 12/2017 | Yang | |
| 2021/0169491 | A1 | 6/2021 | Anderson et al. | |
| 2023/0133253 | A1 | 5/2023 | Shaher | |

* cited by examiner

DEFECT OCCLUDER WITH WRAPPING COVER

RELATED APPLICATION

This application is a continuation of International Patent Application No. PCT/US22/39336, filed Aug. 3, 2022 and entitled DEFECT OCCLUDER WITH WRAPPING COVER, which claims priority to U.S. Provisional Patent Application Ser. No. 63/237,475, filed on Aug. 26, 2021 and entitled DEFECT OCCLUDER WITH WRAPPING COVER, the complete disclosures of which are hereby incorporated by reference in their entirety.

BACKGROUND

Field

The present disclosure generally relates to the field of medical implant devices.

Description of Related Art

Openings and/or other defects can form or otherwise be present in certain biological tissue walls, such as cardiac septa. Such defects can negatively impact physiological function and/or health in some patients and cases.

SUMMARY

Described herein are one or more methods and/or devices to facilitate the treatment of defects in biological tissue, including inventive occluder devices and associated delivery systems and procedures for delivering and deploying the same.

For purposes of summarizing the disclosure, certain aspects, advantages and novel features have been described. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

Methods and structures disclosed herein for treating a patient also encompass analogous methods and structures performed on or placed on a simulated patient, which is useful, for example, for training; for demonstration; for procedure and/or device development; and the like. The simulated patient can be physical, virtual, or a combination of physical and virtual. A simulation can include a simulation of all or a portion of a patient, for example, an entire body, a portion of a body (e.g., thorax), a system (e.g., cardiovascular system), an organ (e.g., heart), or any combination thereof. Physical elements can be natural, including human or animal cadavers, or portions thereof; synthetic; or any combination of natural and synthetic. Virtual elements can be entirely in silica, or overlaid on one or more of the physical components. Virtual elements can be presented on any combination of screens, headsets, holographically, projected, loud speakers, headphones, pressure transducers, temperature transducers, or using any combination of suitable technologies.

BRIEF DESCRIPTION OF THE DRAWINGS

Various examples are depicted in the accompanying drawings for illustrative purposes and should in no way be interpreted as limiting the scope of the inventions. In addition, various features of different disclosed examples can be combined to form additional examples, which are part of this disclosure. Throughout the drawings, reference numbers may be reused to indicate correspondence between reference elements.

FIGS. 3A-1, 3A-2, 3A-3, 3A-4, and 3A-5 illustrate perspective views of a topside of a defect cover in various states of expansion/compression in accordance with one or more examples.

FIGS. 3B-1, 3B-2, 3B-3, 3B-4, and 3B-5 illustrate perspective views of an underside of a defect cover in various states of expansion/compression in accordance with one or more examples.

FIG. 3C-2 illustrates a side cross-sectional view of a defect cover in accordance with one or more examples.

FIGS. 4-1A, 4-1B, and 4-1C illustrate perspective, side, and axial views of a core of an occluder device in accordance with one or more examples.

FIGS. 4-2A, 4-2B, and 4-2C illustrate perspective, side, and axial views of a core of an occluder device in accordance with one or more examples.

FIG. 5 shows a side perspective view of an occluder device in a delivery/compressed configuration in accordance with one or more examples.

FIGS. 10-1, 10-2, and 10-3 provide a flow diagram illustrating a process for implanting an occluder device in accordance with one or more examples.

FIGS. 11-1, 11-2, and 11-3 provide images of cardiac anatomy and certain devices/systems corresponding to operations of the process of FIGS. 10-1, 10-2, and 10-3 in accordance with one or more examples.

DETAILED DESCRIPTION

Figure 1:
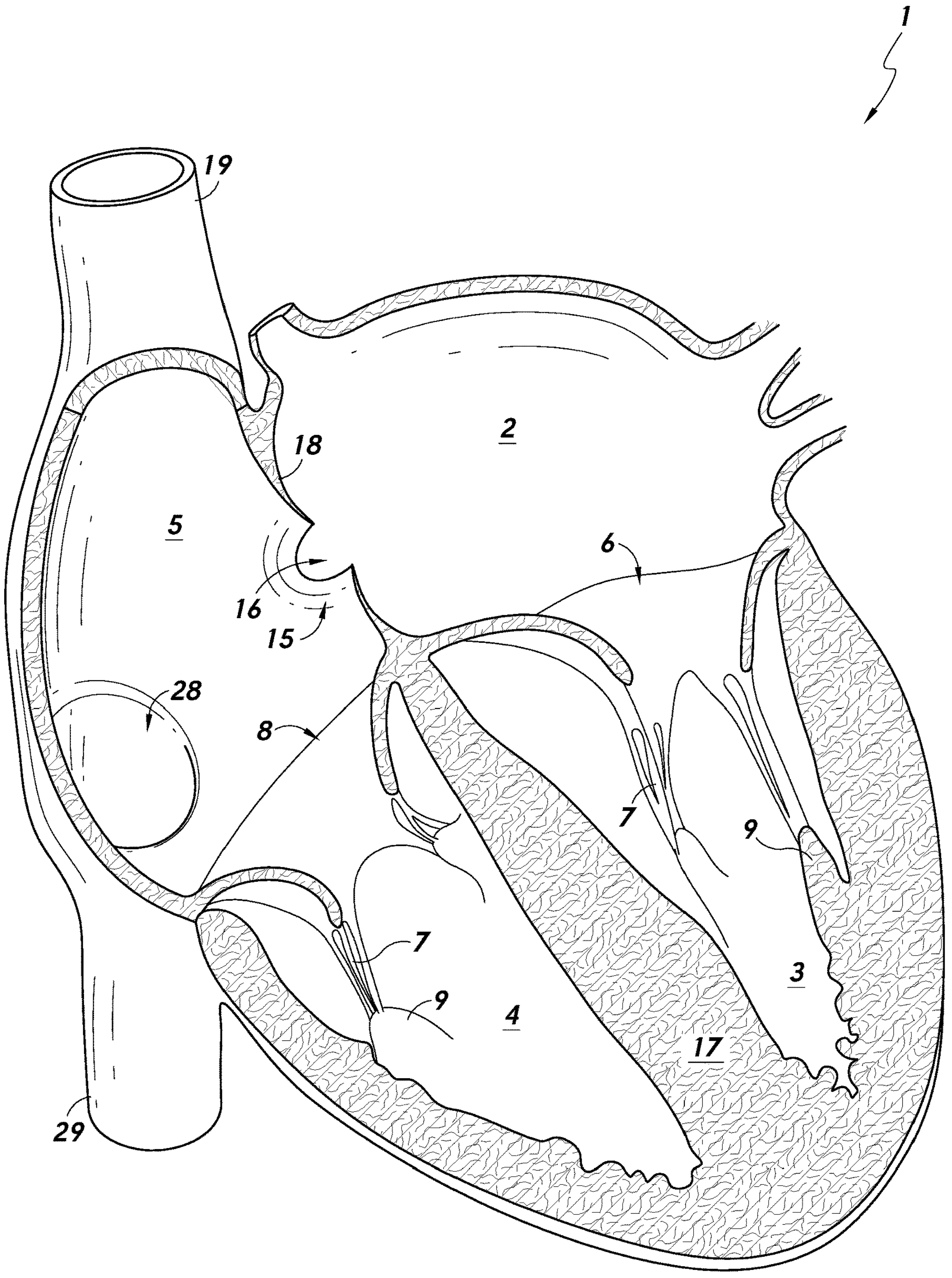
FIG. 1 illustrates an example representation of a human heart in accordance with one or more examples.

The headings provided herein are for convenience only and do not necessarily affect the scope or meaning of the claimed invention.

Although certain preferred examples are disclosed below, inventive subject matter extends beyond the specifically disclosed examples to other alternative examples and/or uses and to modifications and equivalents thereof. Thus, the scope of the claims that may arise herefrom is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain examples;

however, the order of description should not be construed to imply that these operations are order dependent. Additionally, the structures, systems, and/or devices described herein may be embodied as integrated components or as separate components. For purposes of comparing various examples, certain aspects and advantages of these examples are described. Not necessarily all such aspects or advantages are achieved by any particular example. Thus, for example, various examples may be carried out in a manner that achieves or optimizes one advantage or group of advantages as taught herein without necessarily achieving other aspects or advantages as may also be taught or suggested herein.

Certain reference numbers are re-used across different figures of the figure set of the present disclosure as a matter of convenience for devices, components, systems, features, and/or modules having features that may be similar in one or more respects. However, with respect to any of the examples disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another.

Certain standard anatomical terms of location are used herein to refer to certain device components/features and to the anatomy of animals, and namely humans, with respect to the preferred examples. Although certain spatially relative terms, such as "outer," "inner," "upper," "lower," "below," "above," "vertical," "horizontal," "top," "bottom," "under," "over," "topside," "underside," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

The present disclosure relates to systems, devices, and methods for occluding a defect in biological tissue using a septal occluder device having rotationally expansive and compressive cover(s) that provide for a desirably large ratio (e.g., 5:1) between expanded and compressed configurations. In some implementations, the present disclosure relates to occluder devices that include a core form/structure associated with two (e.g., identical) mirrored self-expanding covers including individual radially and/or circumferentially-/rotationally-projecting wires coupled to or otherwise associated with respective coverings (e.g., cloth). Such covers can be configured to progressively transition between and/or assume cylindrical, dish, and/or disc-type forms/configurations through the rotational folding of the cover about an axis of the device. The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Occluder devices of the present disclosure include opposing defect covers coupled by a core form/structure configured to traverse a target defect when the occluder device is deployed/implanted. The use of rotationally-expandable covers in connection with occluder devices as disclosed herein can provide improved compression for reduced delivery configuration profile for transcatheter transportation, as well as sufficient expansion profile/coverage to accommodate coverage of relatively large areas of tissue and/or defects. Furthermore, implementation of partial expansion of such devices/covers, wherein alternating radially-expanding wires of the relevant covers lie in angularly-offset planes, can facilitate conforming of the shape/form of the devices/covers to concave topologies, thereby providing improved fit/sealing. Certain examples of occluder devices are disclosed herein in the context of cardiac implant devices. However, although certain principles disclosed herein are particularly applicable to the anatomy of the heart, it should be understood that occluder implant devices in accordance with the present disclosure may be implanted in, or configured for implantation in, any suitable or desirable anatomy.

Cardiac Physiology

The anatomy of the heart is described below to assist in the understanding of certain inventive concepts disclosed herein. In humans and other vertebrate animals, the heart generally comprises a muscular organ having four pumping chambers, wherein the flow between chambers and vessels associated therewith is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

FIG. 1 illustrates a vertical/frontal cross-sectional view of an example heart 1 having various features/anatomy relevant to certain aspects of the present inventive disclosure. The heart 1 includes four chambers, namely the left atrium 2, the left ventricle 3, the right ventricle 4, and the right atrium 5. In terms of blood flow, blood generally flows from the right ventricle 4 into the pulmonary artery (not shown in FIG. 1 for visual clarity) via the pulmonary valve (not shown in FIG. 1 for visual clarity), which separates the right ventricle 4 from the pulmonary artery and is configured to open during systole so that blood may be pumped toward the lungs and close during diastole to prevent blood from leaking back into the heart from the pulmonary artery. The pulmonary artery carries deoxygenated blood from the right side of the heart to the lungs.

In addition to the pulmonary valve, the heart 1 includes three additional valves for aiding the circulation of blood therein, including the tricuspid valve 8, the aortic valve (not shown in FIG. 1 for visual clarity), and the mitral valve 6.

The tricuspid valve 8 separates the right atrium 5 from the right ventricle 4. The tricuspid valve 8 generally has three cusps or leaflets and may generally close during ventricular contraction (i.e., systole) and open during ventricular expansion (i.e., diastole). The mitral valve 6 generally has two cusps/leaflets and separates the left atrium 2 from the left ventricle 3. The mitral valve 6 is configured to open during diastole so that blood in the left atrium 2 can flow into the left ventricle 3, and, when functioning properly, closes during systole to prevent blood from leaking back into the left atrium 2. The aortic valve separates the left ventricle 3 from the aorta (not shown in FIG. 1 for visual clarity). The aortic valve is configured to open during systole to allow blood leaving the left ventricle 3 to enter the aorta, and close during diastole to prevent blood from leaking back into the left ventricle 3.

The heart valves may generally comprise a relatively dense fibrous ring, referred to as the annulus, as well as a plurality of leaflets or cusps attached to the annulus. Generally, the size of the leaflets/cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage. Disfunction of a heart valve and/or associated leaflets (e.g., pulmonary valve disfunction) can result in valve leakage and/or other health complications.

The atrioventricular (i.e., mitral and tricuspid) heart valves may further comprise a collection of chordae tendineae 7 and papillary muscles 9 for securing the leaflets of the respective valves to promote and/or facilitate proper coaptation of the valve leaflets and prevent prolapse thereof. The papillary muscles 9, for example, may generally comprise finger-like projections from the ventricle wall. The valve leaflets are connected to the papillary muscles by the chordae tendineae 7.

A wall of muscle, referred to as the septum, separates the left-side chambers from the right-side chambers. In particular, an atrial septum wall portion 18 (referred to herein as the "atrial septum," "interatrial septum," or "septum") separates the left atrium 2 from the right atrium 5, whereas a ventricular septum wall portion 17 (referred to herein as the "ventricular septum," "interventricular septum," or "septum") separates the left ventricle 3 from the right ventricle 4. The atrial septum 18 is generally a relatively thin wall tissue, whereas the ventricular septum 17 is typically thicker than they atrial septum 18.

A septal defect or orifice (e.g., atrial septal defect 16) can form in a septal wall in the form of a perforation, aperture, or other hole or passage through the tissue wall. A septal defect can occur congenitally or by puncturing the septum with a medical device to access a location (e.g., left atrium 2) within the heart. While some septal defects can be relatively benign and have relatively little impact on a patient's health, other septal defects can be more serious. Septal defects can result in left-to-right shunting of blood, wherein oxygen-rich blood is shunted to the relatively oxygen-depleted right-side chamber(s) (e.g., right atrium 5). In some cases, such shunting can cause volume overload in the right side of the heart and/or insufficient oxygenated blood being delivered to the body. In some cases, a thrombus or other embolus can travel from the right to the left, potentially causing various health complications, such as migraines and/or stroke.

In some instances, an atrial defect is formed in the area of the fossa ovalis 15, which is a depression in the right atrium 5 of the heart, at the level of the interatrial septum 18. For example, one type of septal defect is a patent foramen ovale (PFO), which is an opening in the area of the fossa ovalis 15. Because the fetal lungs do not provide air prior to birth, fetal blood is oxygenated by the mother in utero via the umbilical cord and placenta. To provide for circulation of such oxygenated blood, the fetal blood circulation system includes certain vessels and openings that are open during fetal development but typically close soon after birth. One such opening is the foramen ovale, a central location in the interatrial septum where the septum primum and the septum secundum overlap, which permits blood to flow from the right atrium into the left atrium in a fetal heart, thereby allowing blood to bypass the fetal lungs and flow directly from the venous circulation to the arterial circulation. After birth, the infant's lungs typically provide oxygenation to the blood, and it is generally undesirable to continue having blood shunt/flow from the venous circulation to the arterial circulation without first passing through the lungs. At birth, left atrial pressure increases as the pulmonary circulation is established. This pressure increase typically causes the closure of a flap of tissue which occludes the foramen ovale and then heals/fixes in the occluded position shortly after birth. The foramen ovale becomes the fossa ovalis depression as the foramen closes.

In some individuals, however, the tissue flap does not heal to permanently occlude the foreman ovale. This condition is known as a patent (i.e., open) foramen ovale (PFO). While a PFO can be a relatively benign condition in some cases, PFOs can lead to migraines and other conditions in some individuals. In some cases, a PFO can cause a stroke by permitting blood containing small thrombi/embolus to bypass the lungs (which would otherwise filter out such small thrombi) and flow directly from the venous circulation to the arterial circulation and ultimately into the brain.

In addition to patent foramen ovale, septal defects can be caused in connection with certain medical interventions. For example, the atrial septum can serve as an access point for certain catheterization procedures for accessing the left atrium from the venous system (i.e., right atrium and inferior or superior vena cava). For example, the atrial septum can serve as a point of percutaneous access for atrial fibrillation therapy, left atrial appendage closure, percutaneous mitral valve repair, and percutaneous mitral valve replacement. In such procedures, devices may traverse across the atrial septum and, by doing so, may leave a defect/opening in the atrial septum that does not close spontaneously.

Health Conditions and Treatments Associated with Septal Defects

As referenced above, defects in cardiac tissue walls, such as patent foramen ovale or other septal defects, can adversely affect the health of an individual. For example, atrial septal defects can cause ischemic stroke due to embolism of venous emboli passing to the arterial circulation from thrombus traversing a patent foramen ovale. In addition, patent foramen ovale can cause migraine headaches in some individuals.

Treatments for patent foramen ovale (PFO) and other septal defects can include open-heart surgery, as well as percutaneous (e.g., transcatheter) procedures. Open-heart surgery for septal defect closure can involve suturing the opening/defect closed. Such open-heart surgical treatment can be associated with a variety of risks typically associated with cardiac surgery. Percutaneous methods can involve deploying mesh, clamshell, plug, or other similar implanted devices to close the opening. Other treatments can include using heat, laser, RF, or other energy to treat the tissue of (or adjacent to) the septal defect to induce the tissue to permanently close the opening. Such percutaneous methods can be complicated and/or involve relatively large implant devices or uncertain tissue treatments. In some cases, the implantation of a septal defect closure device forecloses the ability to re-cross the septum in connection with a subsequent intervention. Septal defect closure devices can be implanted percutaneously, such as through femoral venous puncture/access. Such procedures can be guided by echocardiography.

Defect Occlusion Devices Including Rotationally-Expandable/Compressible Covers

As referenced above, the treatment of septal defects can involve the implantation of devices designed to occlude, or cover, the septal defect. Disclosed herein are novel occluder devices including rotationally foldable septal defect covers configured to be transported to a target treatment site in a folded configuration within a delivery sheath or catheter and expanded upon deployment from the delivery sheath/catheter. Such foldable covers can be configured to form radial/transverse pleats or other types of corrugations that can be circumferentially/rotationally wrapped around an axis of the cover, wherein such pleats/corrugations are formed by alternating 'mountain' (e.g., 'peak,' 'crest,' or the like) and 'valley' (e.g., 'trough,' or the like) radial and/or circumferentially/rotationally curved folds/creases in the cover. The folds can be along individual wires or wire segments, as described in detail herein.

Figure 2:
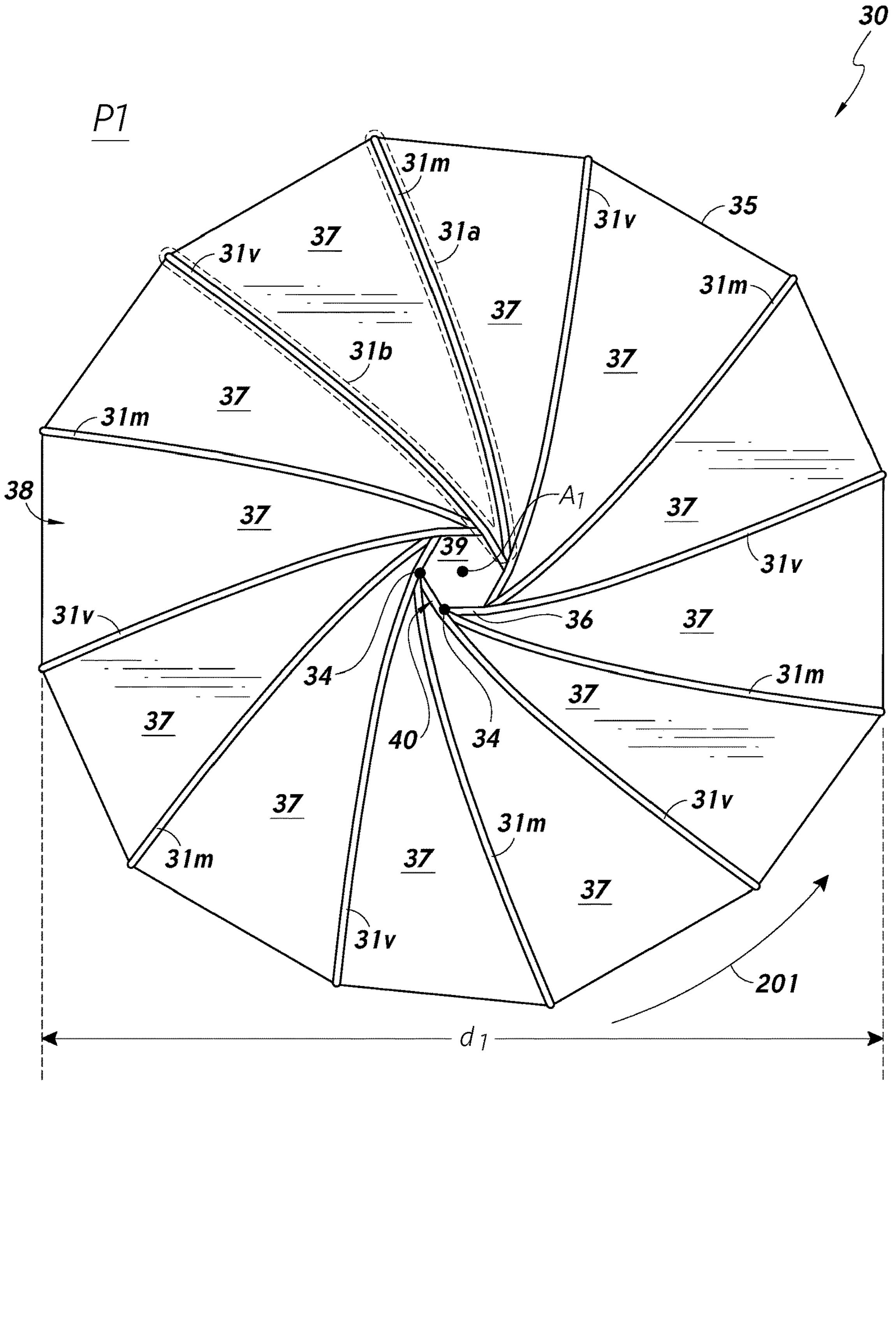
FIG. 2 illustrates a defect cover in a flat configuration in accordance with one or more examples.

FIG. 2 illustrates a defect cover 30 that may be used in connection with a defect occluder device in accordance with the present disclosure, wherein the cover 30 is shown in a fully-expanded and/or flat configuration. The cover 30 may be one of two mirrored cover components of an occluder device, wherein the cover 30 may be configured to be deployed on one side of a tissue wall in which a defect is present, such as an atrial or ventricular septum wall. In some implementations, the defect cover 30 is configured to be folded in an origami-style manner, wherein creases in the cover create major fold lines to allow for compression and expansion of the cover in a manner such that the cover forms a cylindrical form in the compressed state, a substantially flat disc in the expanded configuration, and a disc- and/or dish-shaped form having radial ridges with mountain and valley folds in intermediate expansion/compression states between the fully-expanded state shown in FIG. 2 and the cylindrical fully compressed state (see FIGS. 3A-5 and 3B-5). The fold lines, which may be along and/or about radially-projecting wires 31, can radiate outward from a central/core portion 39. In some examples, the fold lines further curve circumferentially/rotationally as they move radially outward, as shown. That is, the fold lines and/or associated wires 31 can radiate outward and curve with left- or right-handed chirality. With respect to wires and folds of covers disclosed herein, rotational and/or circumferential curvature and/or wrapping can be understood to be in a direction about an axis $A_1$ of the cover, such as in the direction 201 shown in FIG. 2, or in a direction opposite the direction 201.

Certain septal defect cover solutions can include wire-frame designs that are relatively intricate and/or bulky, wherein such covers have difficulty adapting to the curvature/topology of the septum or other tissue wall. In some examples, each of the wire segments 31 are separate wires and/or configured to be independently or individually manipulable/movable. Use of individual radiating wires can advantageously allow for the cover 30 to contour the septum or other tissue wall. The wires 31 are fixed at their base to the central/core portion 39 and configured to twist/wrap around the axis $A_1$ of the cover 30. Such system of wires can provide desirable flexibility to allow the cover 30 to adapt to various shapes and surfaces.

The covering 38 can be a single cloth or can be made up of multiple at least partially fluid-tight segments/cloths. In the image of FIG. 2, the illustrated wires/wire segments 31 can be understood to represent fold lines, or potential fold lines, in the cover 30. The wires/folds $31_m$ can be folded as mountain/peak folds, whereas the wires/folds $31_v$ can be folded as valley folds, or vice versa. That is, the wires/folds $31_m$ and $31_v$ can include bends/apices that point in distal (e.g., out of the page with respect to the orientation of FIG. 2) and proximal (e.g., into the page with respect to the orientation of FIG. 2) directions, respectively. With respect to defect covers of the present disclosure, description of the same as being "substantially flat" in an expanded configuration, as in FIG. 2, may be understood to refer to the cover in a completely flat configuration in which the mountain $31_m$ and valley $31_v$ wires and folds are co-planar, or may refer to a state in which the mountain $31_m$ wires/folds are slightly angled relative the valley $31_v$ wires/folds, wherein such angle is less than or equal to 15°, or less than or equal to 30°, with respect to an axial plane of the cover and/or associated occluder device (e.g., the plane of the page with respect to the image of FIG. 2).

The cover 30 includes a central portion 39, which may be hexagonal in shape, or have any other shape or size/area. The central portion 39 of the cover 30 may be part of the cloth or other material of the covering 38; that is, the central portion 39 may be a central portion of the covering 38 of the cover 30. The central portion 39 may be an axial end of a core form associated with the cover 30. In some examples, the central portion 39 does not include any folds, but rather the 'petals' of the folding pattern of the covering 38 fold according to right- or left-handed chirality around the central portion 39, wherein the term 'petals' may be used to refer to one or more of the wires 31 and interposed or adjacent segments 37 of the covering 38. For example, a 'petal,' or 'wire,' as described herein, may refer to either a mountain $31_m$ or valley $31_v$ wire together with one or both adjacent covering segments 37. In examples including more (or fewer) petals/wires than shown in FIG. 2, the shape of the central portion 39 may have more (or fewer) sides than six. The central portion 39 may be disposed on or over a structural core form/component of an occluder device. References herein to a central portion of a covering may be understood to refer to a core component of an occluder device, and vice versa, and any description herein of either component may be understood as being a description of the central portion of the covering, the core (e.g., the end/cap portion of a core component), or both.

The cover 30 can expand to a really large diameter $d_1$ and can also be compressed to a much smaller profile in a folded, cylindrical configuration for delivery. For example, the cover 30 may advantageously be configured to expand to an expanded, substantially flat configuration, as shown in FIG. 2, while further being configured to be compressed to a diameter significantly smaller than the expanded diameter $d_1$ of the cover 30 in the expanded configuration. The cover 30 may be configured to be compressed/folded in a manner as to form a generally cylindrical shape, wherein the cylinder has a diameter dimension that is less than or equal to 25% of the expanded diameter $d_1$ of the cover 30. For example, the ratio between the expanded diameter $d_1$ and the compressed/folded diameter $d_2$ (see FIGS. 3A-5 and 3B-5) of greater than about 4:1, 9:2, 5:1, 11:2, 6:1, or greater. For example, in some examples, the ratio $d_1$:$d_2$ is 5:1.

The cover 30 includes a cloth, polymer, and/or tissue covering material 38, which may be fluid tight in some implementations. In some examples, the covering 38 comprises a mesh, such as a wire mesh, suture mesh, mesh of polymer fibers/strands, and/or the like. Generally, the covering 38 may serve to occlude the defect/feature over which it is placed, thereby at least partially preventing or reducing the passage of fluid through the defect when the cover 30 is in place.

The cover 30 can include a plurality of wires 31. Although described as wires herein, it should be understood that such features of a cover in accordance with aspects of the present disclosure may be or comprise any type of elongate arm structure, such as a wire, band, suture, rod, pole, stick, line, shaft, or the like, wherein such arms are attached to and/or otherwise associated with the covering 38 in some manner. For example, the wires 31 may be threaded/woven through portions of the covering 38 in a generally radial direction, or may be sutured, adhered, or otherwise coupled to the covering 38. In some examples, the wires 31 are attached to the covering 38 only at distal ends thereof and/or proximal ends thereof. For example, the distal end of a wire 31 may be coupled to a portion of the perimeter 35 of the covering 38.

The wires 31 may further be coupled at proximal ends thereof to a core form or other component/feature of an occluder device. With respect to the description of the wires 31, 'proximal' refers to an innermost portion or end of a wire, such as a portion of the wire that is at or near the central axial portion/core 39 of the cover 30. For example, the wires 31 may be configured to hook onto the core/portion 39 in some manner. For example, the proximal portions of the wires 31 may include hooks that are configured to couple to corresponding loops or other features associated with a core component/form (see, e.g., FIGS. 4-1A-C, 4-2A-C). In some examples, the proximal ends of the wires 31 are press-fit into the core. For example, the core may include certain tapered slots or other features configured to receive and hold proximal portions of the respective wires 31.

The wires 31 may each be independent wires or wire segments. For example, each of the wires 31 may be configured to move independently of any of the other wires/segments 31. In some examples, multiple wire segments may be formed of a single wire. That is, different wire segments may be segments of the same wire. For example, with further reference to FIG. 2, the illustrated wire segment 31*a* may represent half of a wire, wherein the second half of the wire forms the wire segments 31*b*. However, it should be understood that wire segments 31 can be combined with any number of other wire segments in a single integrated wire. Although folding/bending of wires for the purpose of implementing multiple wire segments from a single wire may be implemented in accordance with examples of the present disclosure, it may be advantageous to instead use physically separate wires for each of the wire segments 31 of the cover 30. Implementing two wires for every vertex/side of the cross-sectional/end shape of the core/portion 39 can facilitate secure anchoring of the wires 31 to the core/portion 39.

As described above, the central portion 39 of the cover may be, or be associated with, an axial end of a core form, which may have a polygonal shape, as shown. Generally, the wire segments 31 may emanate radially outward from a perimeter 36 of the end/portion 39 of the core 40 (see, e.g., FIGS. 4-1A-C, 5, 7A, 7B). The core 40 may comprise a structure or form configured to connect a first cover 30 with a second cover (not shown) of a dual-cover occluder device, as described in detail herein. In some examples, the core 40 has axial end caps/portions 39 that have a polygonal shape including a finite number of straight, or substantially straight, sides 36, as with the illustrated hexagonal core shape 39 shown in FIG. 2. Although a hexagonal core 40 is shown, wherein description of the shape of a core in the present disclosure may refer to an axial cross-sectional shape of at least a portion of the core, it should be understood that examples of occluder device cores in accordance with aspects of the present disclosure may have any type of polygonal shape. Furthermore, although the core 40 is shown as having a polygonal shape with straight sides forming the perimeter thereof, it should be understood that in some examples, a core of an occluder device in accordance with aspects of the present disclosure can have sides that are at least partially curved, either in a concave or convex manner. Furthermore, in some examples, the core 40 may have a circular or other elliptical shape. That is, it is not necessary that the core 40 have straight sides.

In some examples, such as in the example of FIG. 2, the number of wires/wire segments 31 is equal to a multiple of the number of sides and/or points/vertices 34 of the shape 39 of the core 40. For example, as shown in FIG. 2, where a hexagonal core 40 is implemented, the number of wires 31 may equal a multiple of six, wherein six corresponds to the number of sides 36 of the hexagonal core 39, as well as the number of points/vertices 34 at the interfaces/junctures between adjacent sides. In particular, in the example of FIG. 2, the number of wires 31 is equal to two times the number of sides/vertices of the shape 39. Implementing two wires for each side/vertex of the polygonal shape of the core 40 may be advantageous for various reasons. For example, such number of wires 31 may provide sufficient structural support for the covering 38, while not introducing too much structure to the design of the cover 30 to overly impair the ability of the cover to be compressed to a desirably small profile for delivery of the cover 30 and associated device. Furthermore, the geometry of the polygonal shape 39 may be conducive to the presence of two wires for every side/vertex of the shape. For example, when emanating from the central core 40, the wires 31 may alternatingly emanate from a vertex 34 and run along an adjacent side 36 of the shape 39, whereas the alternating adjacent wire(s) may emanate from the same vertex 34, while radiating away from the adjacent side 36. Although FIG. 2 shows alternating wires $\mathbf{31}_m$ as running along sides 36 of the polygon shape 39 at proximal portions thereof, it should be understood that in some examples, each wire 31 emanates and radiates from a vertex 34 without running along one of the sides of the polygonal shape 39. In some examples, the mountain fold wires $\mathbf{31}_m$ run along the sides the geometric shape 39, whereas the valley fold wires $\mathbf{31}_v$ radiate outward from the core without running alongside a side of the geometric shape, or vice versa.

The covering 38 may be disposed over one or more of the wires 31 and/or the end 39 of the core 40. Alternatively, the covering 38 may be disposed at least partially under the wires 31 and/or around the core 40 without covering the end the core 40. In some examples, the valley fold wires $\mathbf{31}_v$ are disposed over the covering 38, whereas the mountain fold wires $\mathbf{31}_m$ are disposed under the covering 38, or vice versa, which may allow the covering 38 to fold around the wires as desired.

As referenced above, the wires/segments 31 may facilitate folding/compression of the cover 30 about the core 40. In order to facilitate such folding, alternating ones $31_v$ of the wires 31 may serve as valley fold wires, wherein such wires are wrapped circumferentially around the core 40 during compression in or relatively near a plane $P_1$ (e.g., a plane in which the expanded/flat cover 30 lies when expanded as shown in FIG. 2), whereas alternating wires $31_m$ interleaved between the valley fold wires $31_v$, referred to herein as a mountain fold wires $31_m$, wrap circumferentially around the axis $A_1$ of the core 40 in a manner as to wrap circumferentially and project axially away from the core 40 and/or plane $P_1$ (e.g., in a direction out of the page with respect to the illustrated orientation of FIG. 2) to allow for the folds of the covering 38 to wrap circumferentially around the axis $A_1$ of the core 40. For example, when being compressed, the portions/segments 37 of the covering 38 between adjacent wires may alternatingly fold in a manner such that alternating covering portions 37 face in opposite directions circumferentially (see, e.g., FIGS. 3A-4, 3B-4, 3A-5, and 3B-5). In some examples, the covering 38 is disposed over the mountain fold wires $31_m$ (i.e., in front of the mountain fold wires $31_m$ with respect to the illustrated orientation of FIG. 2) and under the valley fold wires $31_v$(i.e., behind the valley fold wires $31_v$ with respect to the illustrated orientation of FIG. 2). Such alternating placement of the wires over and under/behind the covering 38 may facilitate the mountain-valley folding shown and described herein.

The segments 37 of the covering/cloth 38, at the outer perimeters thereof, may be substantially straight between the adjacent wires 31, as shown in the illustrated example of FIG. 2. Alternatively, the perimeter portions 35 between adjacent wires may be curved, or even circular with respect to the arclength thereof. That is, although the cover 30 is illustrated as having a polygonal shape when flattened-out as shown in FIG. 2, it should be understood that in some examples, the cover 30 may be circular or other elliptically shaped.

Although the cover 30 is described with respect to the configuration of FIG. 2 as being substantially flat in a fully-expanded configuration, it should be understood that covers described herein as flat, or substantially flat, in their fully-expanded covers may not be co-planar or parallel with an axial plane $P_1$ of the cover, but rather may have some amount of axial deflection to produce a concavo-convex dish-/disc-type form in the fully-expanded state. Such concavity/convexity, as described in detail herein, may allow for the cover to conform to a concave tissue topology to produce an improved fit/seal of the cover against the target tissue wall. In fully-expanded configurations in which the wires are axially deflected, the mountain and valley fold wires may nevertheless lie substantially in a common conical plane that is angled with respect to the axial plane of the cover.

FIGS. 3A-1, 3A-2, 3A-3, 3A-4, and 3A-5 illustrate perspective views of a topside of a defect cover 30 in various states of expansion in accordance with one or more examples. FIGS. 3B-1, 3B-2, 3B-3, 3B-4, and 3B-5 illustrate perspective views of an underside of the defect cover 30 in various states of expansion in accordance with one or more examples.

With respect to foldable defect covers disclosed herein, references herein to a topside thereof may generally refer to an axial side of the cover associated with the concavity of the cover when folding. That is, as described in detail herein, when folded/compressed, a cover in accordance with aspects of the present disclosure may include mountain fold wire segments $31_m$ that project axially away from a center/core 39 of the cover in a given axial direction. The topside of the cover may be considered to be the side of the cover associated with the axial direction of bending/folding of the mountain fold wires $31_m$. With respect to dual-cover occluder devices in accordance with aspects of the present disclosure, the topside of such covers refers to the sides of the covers that face axially outward, away from an axial center of a core of the device. Conversely, the underside of a defect cover as described herein may generally refer to an opposite axial side of the cover from the topside. That is, the underside of a cover may generally be associated with the convexity of the cover as it folds, such that the underside is a perspective from a side of the cover away from which the mountain fold wires project as they are folded/wrapped circumferentially around the core 39 and project radially away from the core. With respect to dual-cover occluder devices in accordance with aspects of the present disclosure, the underside of such covers refers to sides of the covers that face axially inward, in the direction of an axial center of a core of the device.

Figures 1, 3B:
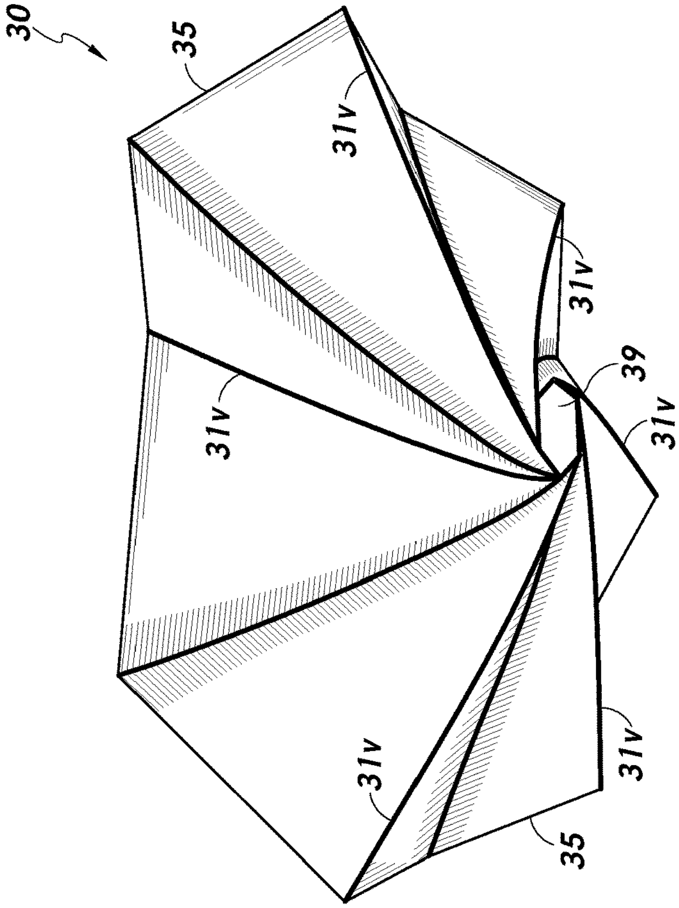
Figures 1, 3A:
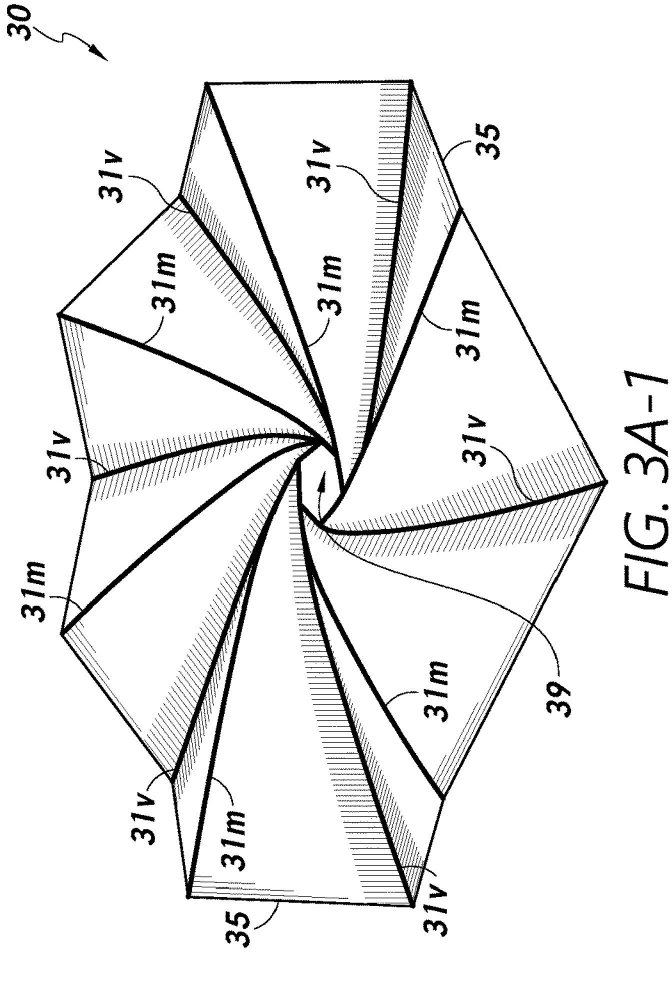
Figures 2, 3B:
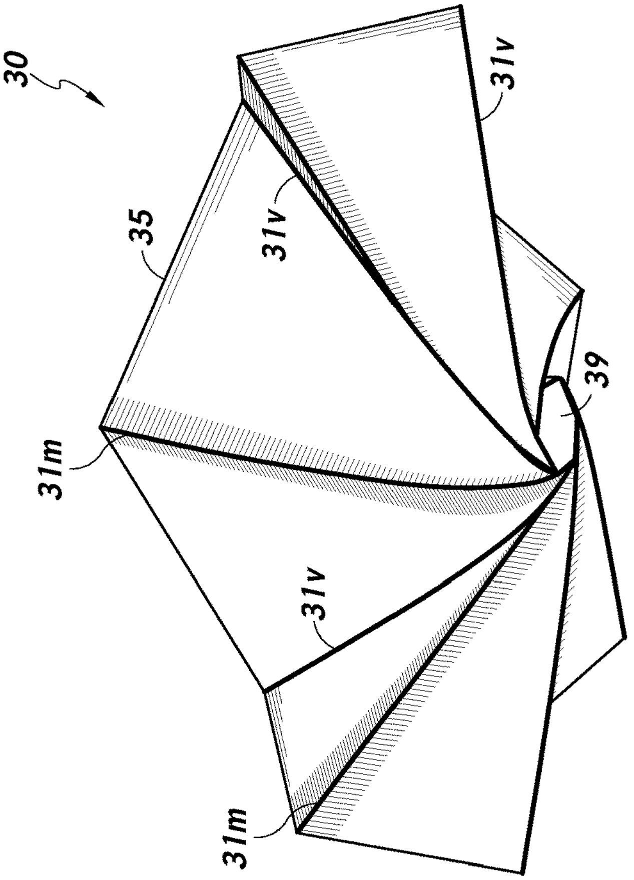
Figures 2, 3A:
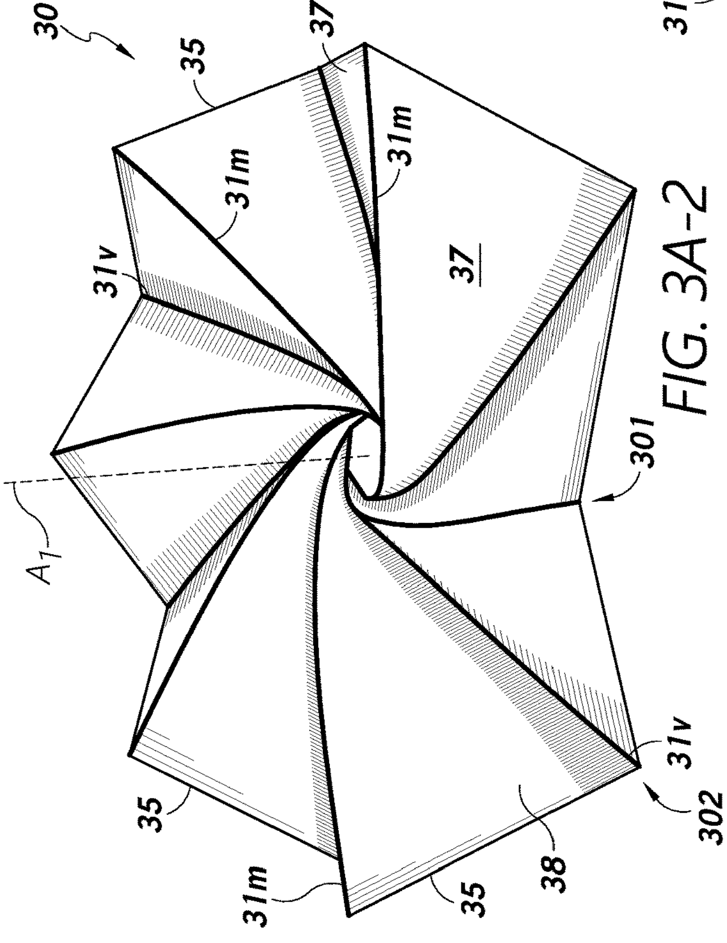

FIGS. 3A-1 and 3B-1 show a partial state of compression of the cover 30, wherein such state shown may correspond to an intermediate stage of a compression process for folding/compressing the cover 30 for delivery thereof, or may represent an intermediate expansion/compression stage that serves as a desired deployment configuration of the cover 30. For example, in some cases, it may be desirable to deploy the cover 30 against a tissue wall and/or cover a defect in such wall, wherein the cover is not completely flat/expanded, but rather has some degree of folding/compression to produce a shape thereof that is dish-like, having a convexity producing an apex at or near the central core/portion 39 and fanning-out in an at least partially concave and/or conical form. Such dish-like shape may be better suited for some anatomy compared to entirely flat configurations, particularly when the anatomy (e.g., tissue wall) presents certain concave topology and/or features that conform better to the partially compressed/folded state shown in FIGS. 3A-l and 3B-1 (or any of FIGS. 3A-2, 3B-2, 3A-3, 3B-3) than to the flat configuration shown in FIG. 2.

As is apparent in the images of FIGS. 3A and 3B, as the cover 30 is folded, the mountain fold wires $31_m$ produce peaks flanked on either side by the segments 37 of the covering 38, which deflect downward from the peak in opposite directions from the wire $31_m$. In a similar manner, the valley fold wires $31_v$ form valleys/troughs flanked on either side by segments 37 that rise to meet respective ones of the mountain fold wires $31_m$ in opposite directions.

Generally, the valley fold wires 31~ may wrap circumferentially around the central portion/core 39 generally in plane with the center/core 39 when fully compressed as shown in FIGS. 3A-5 and 3B-5. For example, when fully compressed, the valley fold wires $31_v$ may generally be substantially co-planar with the base of the cover 30. However, during certain intermediate expansion stages as shown in the remaining images of FIGS. 3A, 3B, and 3C, the valley fold wires $31_v$ may have some amount $\theta_1$ of axial deflection away from the base, thereby producing a concave/dish-type shape, which can advantageously conform to the topology of the fossa ovalis or other anatomy. When the valley fold wires $31_v$ are axially deflected by an amount $\theta_1$, the cover can form a concavo-convex dish-/disc-type form configured to nest in an at least partially concave tissue surface.

Figures 2, 3C:
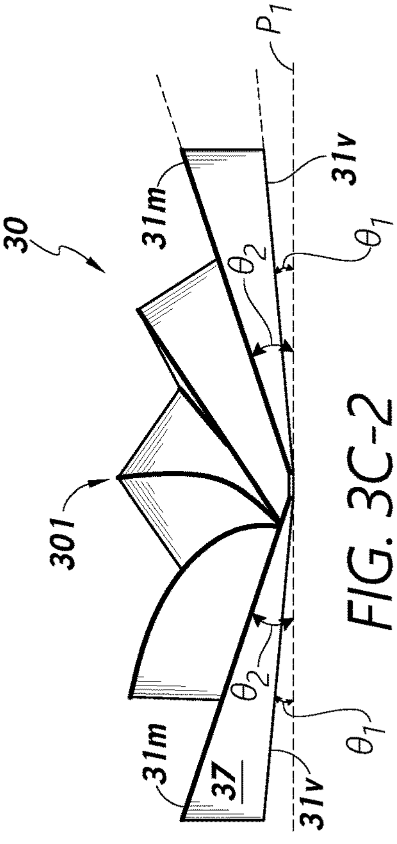
Figures 3, 3B:
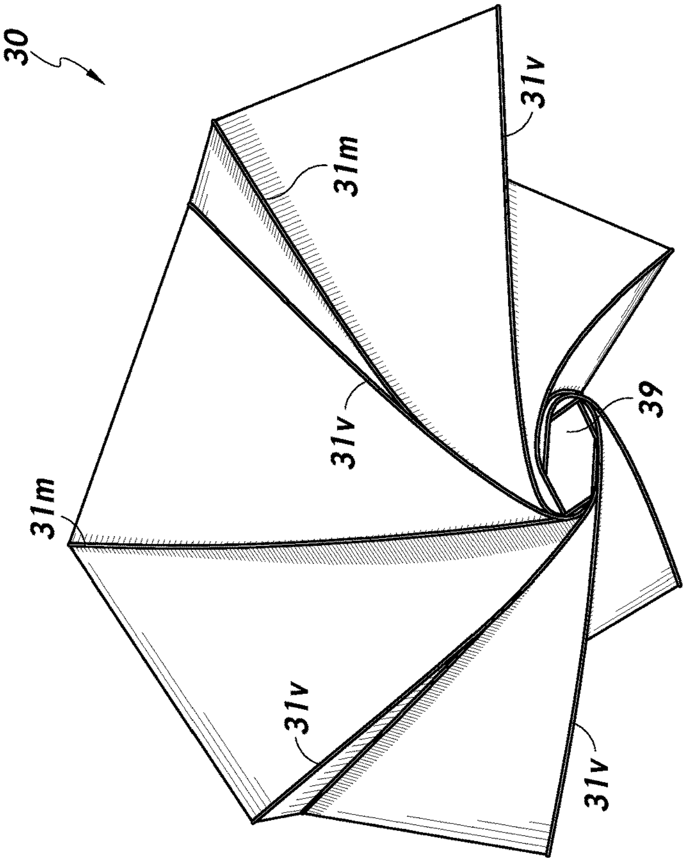
Figures 3, 3A:
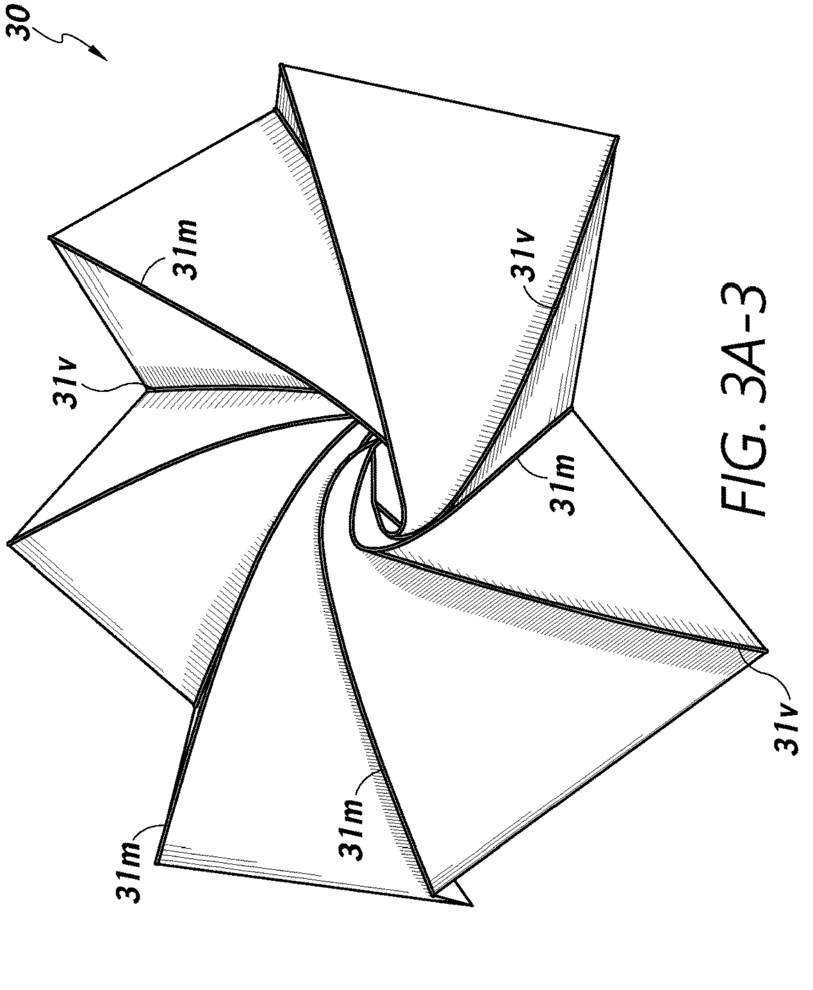

In the partially-expanded configuration of FIG. 3C-2, the valley fold wires $31_v$ may be axially deflected by an amount 61 relative to the axial plane $P_1$, wherein $\theta_1$ may be between 0°-15°, whereas the mountain fold wires $31_m$ may be axially deflected by an amount $\theta_2$ that is greater than the deflection $\theta_1$ of the valley fold wires, as shown.

Although the images of FIGS. 3A and 3B show the respective wires wrapping circumferentially around the central portion 39 in a left-handed direction with respect to the top view images of FIG. 3A, it should be understood that in some examples, the wires 31 may wrap in the opposite direction around the center 39 and/or core 40 (not shown in FIGS. 3A and 3B). That is, the wires 31 may be configured to wrap/fold around the center 39 and/or core 40 according to either right-handed or left-handed chirality. The images of FIGS. 3A and 3B show the central portion 39, which may be a portion of cloth of the covering 38, or may represent an axial end of the core form associated with the cover 30. In some examples, the illustrated cover 30 is one cover of a dual-cover occluder device as described in detail herein.

FIGS. 3A-5 and 3B-5 show the cover 30 in a fully compressed configuration/state, in which the cover 30 forms an at least partially cylindrical shape/form, wherein portions of the segments 37 of the covering 38 between the wires 31 form the walls of the cylinder. The cover 30, in its compressed/cylindrical configuration can advantageously have a reduced profile/diameter $d_2$ compared to the expanded diameter $d_1$ shown in FIG. 2. In some examples, the low-profile diameter $d_2$ of the cover 30 in the compressed/delivery configuration shown in FIGS. 3A-5 and 3B-5 is less than or equal to 25% of the dimension of the expanded diameter $d_1$ of the cover 30 in its expanded/flat state shown in FIG. 2. With respect to the compressed configuration top view image of FIG. 3A-5, such configuration may be referred to herein as having a closed 'flower' shape/configuration, wherein the expansion of the cover 30 from such configuration, as shown in FIGS. 3A-4, 3B-4, 3A-3, 3B-3, 3A-2, 3B-2, 3A-1, and 3B-1 may represent the gradual/incremental opening of the 'flower' form, potentially ultimately resulting in the flat configuration of FIG. 2, or expansion of the cover 30 may complete/end at an intermediate state associated with one of the sets of images of FIGS. 3A and 3B.

As the cover 30 is gradually compressed, the covering 38 is folded over/around the wires 31 to form radially- and/or circumferentially-oriented pleats, corrugations, grooves, crimps, ridges, flutes, or similar features that collapse together as they wrap around the axis $A_1$ of the cover 30. The apices of the pleats alternate between mountain 301 and valley 302 points, as shown, creating a chevron, or zig-zag, circumference/perimeter 35 with reducing angles as the pleats wrap tighter around the core.

A slightly- or partially-compressed defect cover, such as shown in FIGS. 3A-1, 3B-1, and/or 3A-2, 3B-2 can produce a shape of the cover 30 that is configured to contour the atrial septum or other tissue wall against which the cover 30 is intended to be disposed. For example, the atrial septum may generally have certain natural concavity on one or more sides thereof. The atrial septal wall can cave-in towards a relatively thinner layer of tissue associated with the fossa ovalis. With respect to patent fossa ovalis conditions, such openings or gaps in the septum may comprise a hole through the fossa ovalis portion of the septal wall or a plurality of flaps that are overlapping by some amount. By positioning a defect cover in accordance with aspects of the present disclosure such that it is outwardly concave (e.g., dish-shaped with the apex thereof directed towards the septal wall), the corresponding inward convexity can fit and/or account for the septal wall concavity.

Because the size of the atrial septum can vary significantly across patients, deploying occluder devices in accordance with aspects of the present disclosure in configurations in which one or more of the covers thereof is partially compressed/folded, as in some of the images of FIGS. 3A and 3B, the occluder device can be tailored to fit relatively smaller septa or tissue anatomy. Furthermore, when the cover(s) of an occluder device in accordance with aspects of the present disclosure is fully expanded, or mostly expanded, such cover can cover a relatively large area of tissue wall, including possibly covering substantially the whole septal wall for some patients, wherein such expansive coverage may be achievable while still allowing for a relatively small profile for delivery and for traversal of the defect/hole in the tissue wall. That is, it may not be necessary to create a large hole in the area of the defect in order to accommodate an occluder device that is capable of substantial expansion/coverage.

In some implementations, septal closure/occluder devices in accordance with the present disclosure include two covers configured to be folded/pleated as shown in FIGS. 3A and 3B. Such covers may be substantially identical, wherein the two covers are configured to close a septal defect on opposite sides of the tissue wall. In some examples, the covers are self-expanding, such that they automatically fold out when deployed from the delivery catheter.

Figures 3, 3B, 4:
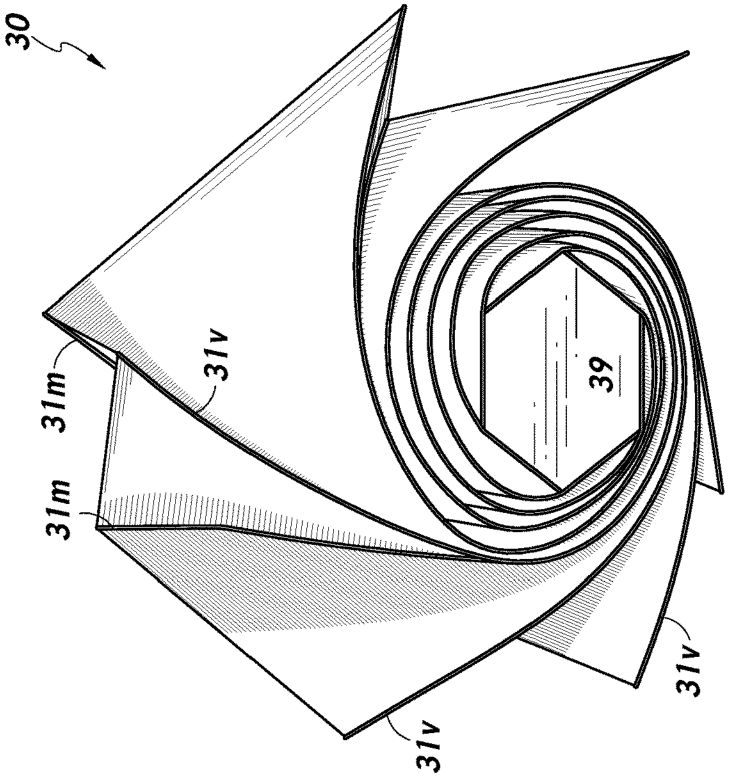
Figures 3, 3A, 4:
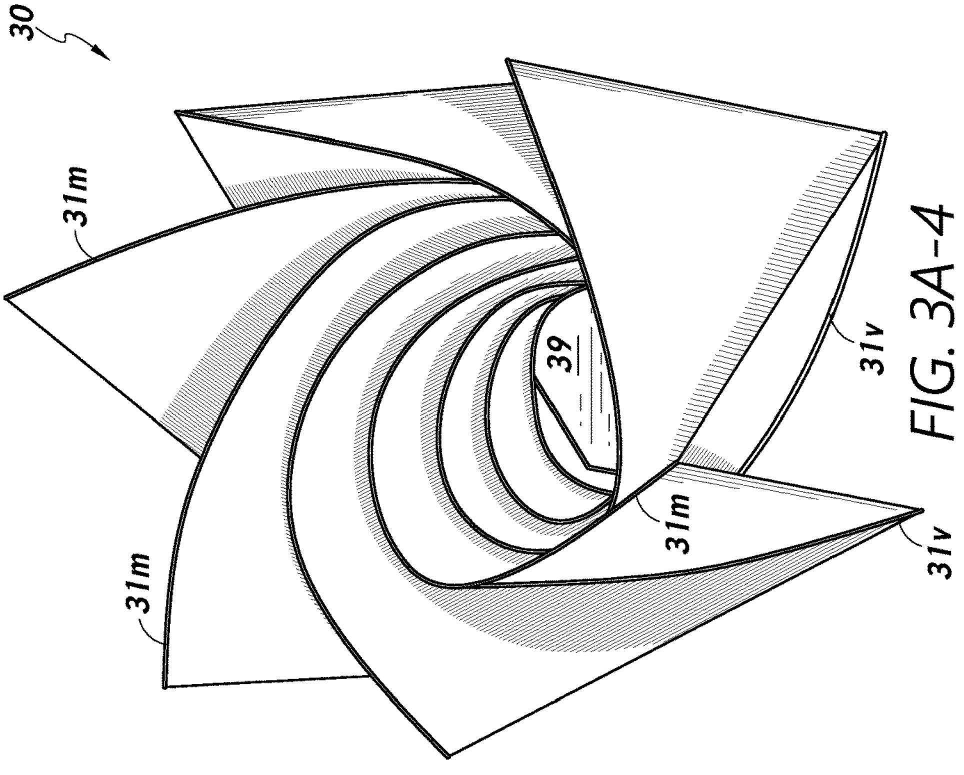
Figures 1B, 4:
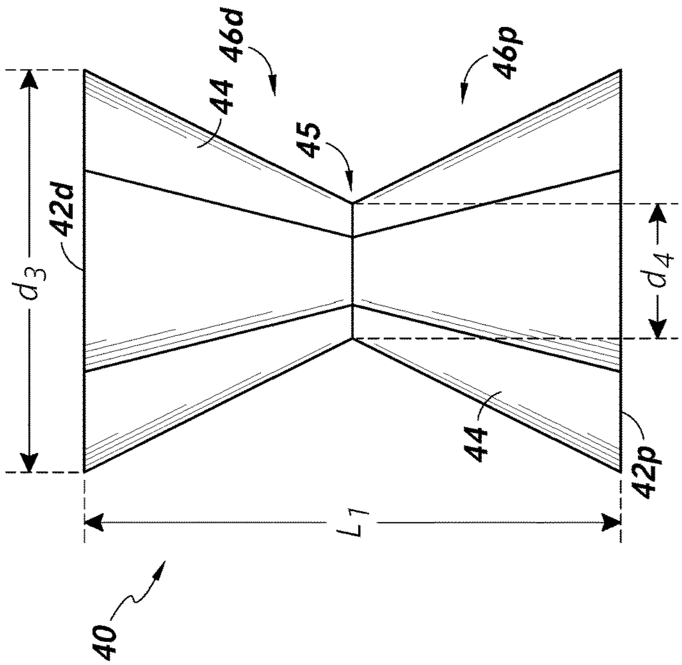
Figures 1A, 4:
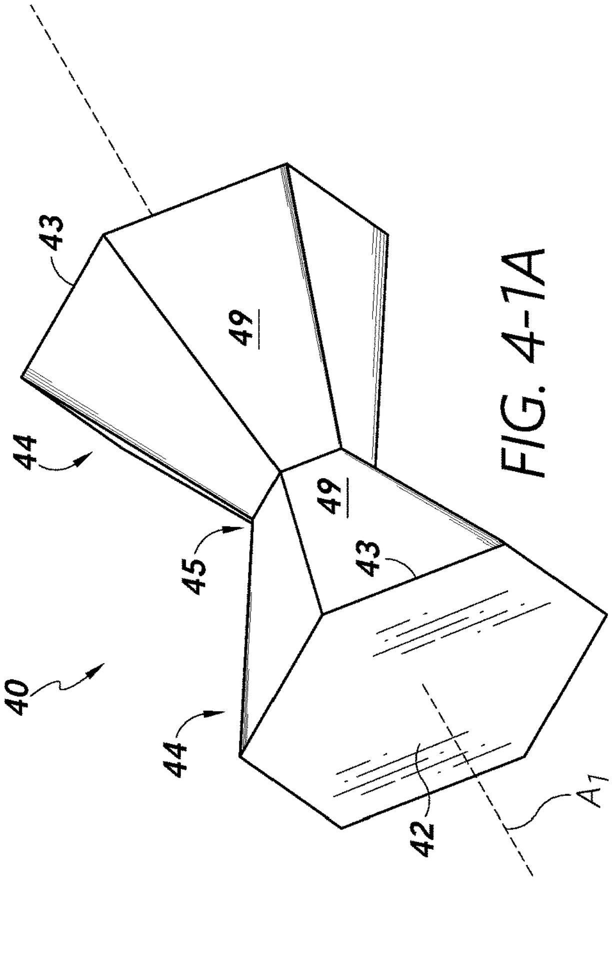
Figures 1C, 4:
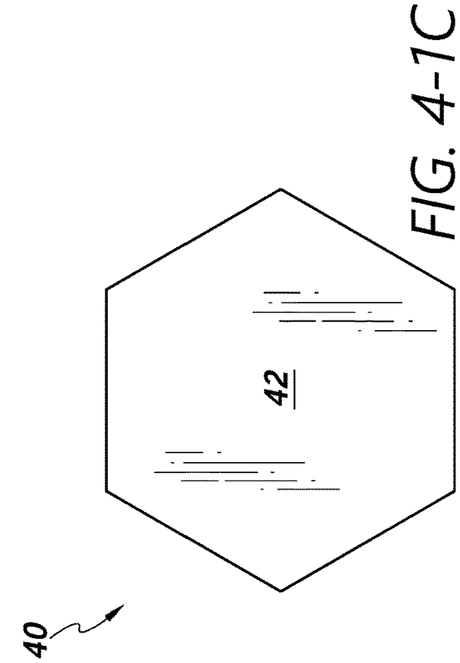
Figures 2B, 4:
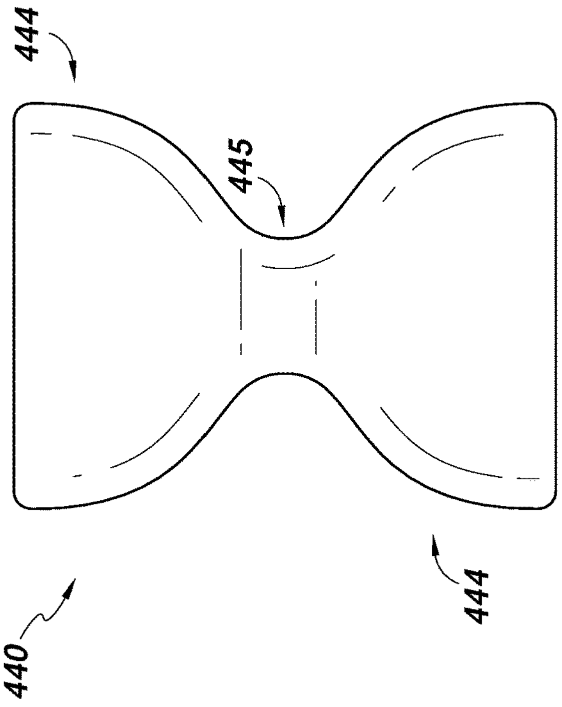
Figures 2C, 4:
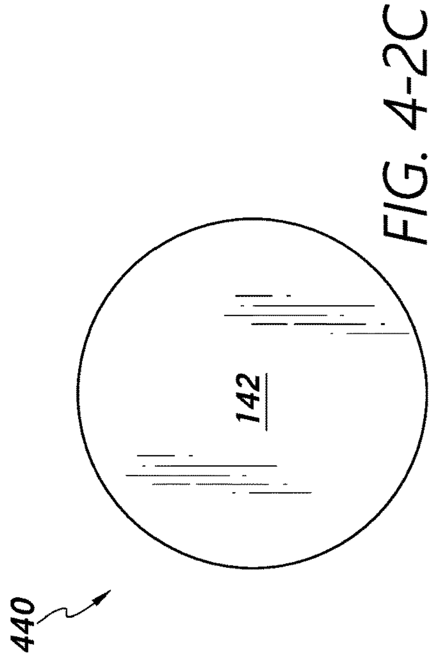
Figures 2A, 4:
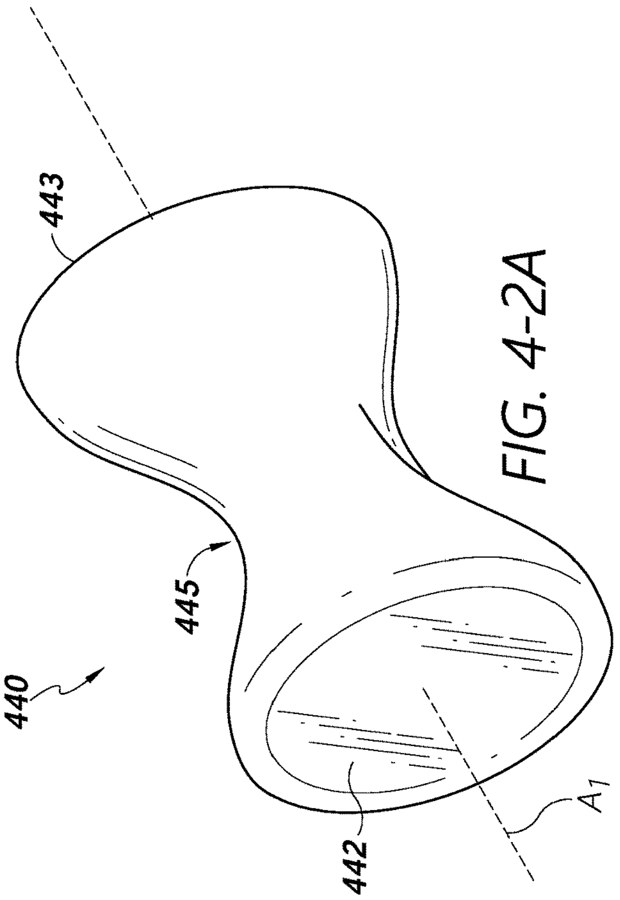
Figure 5:
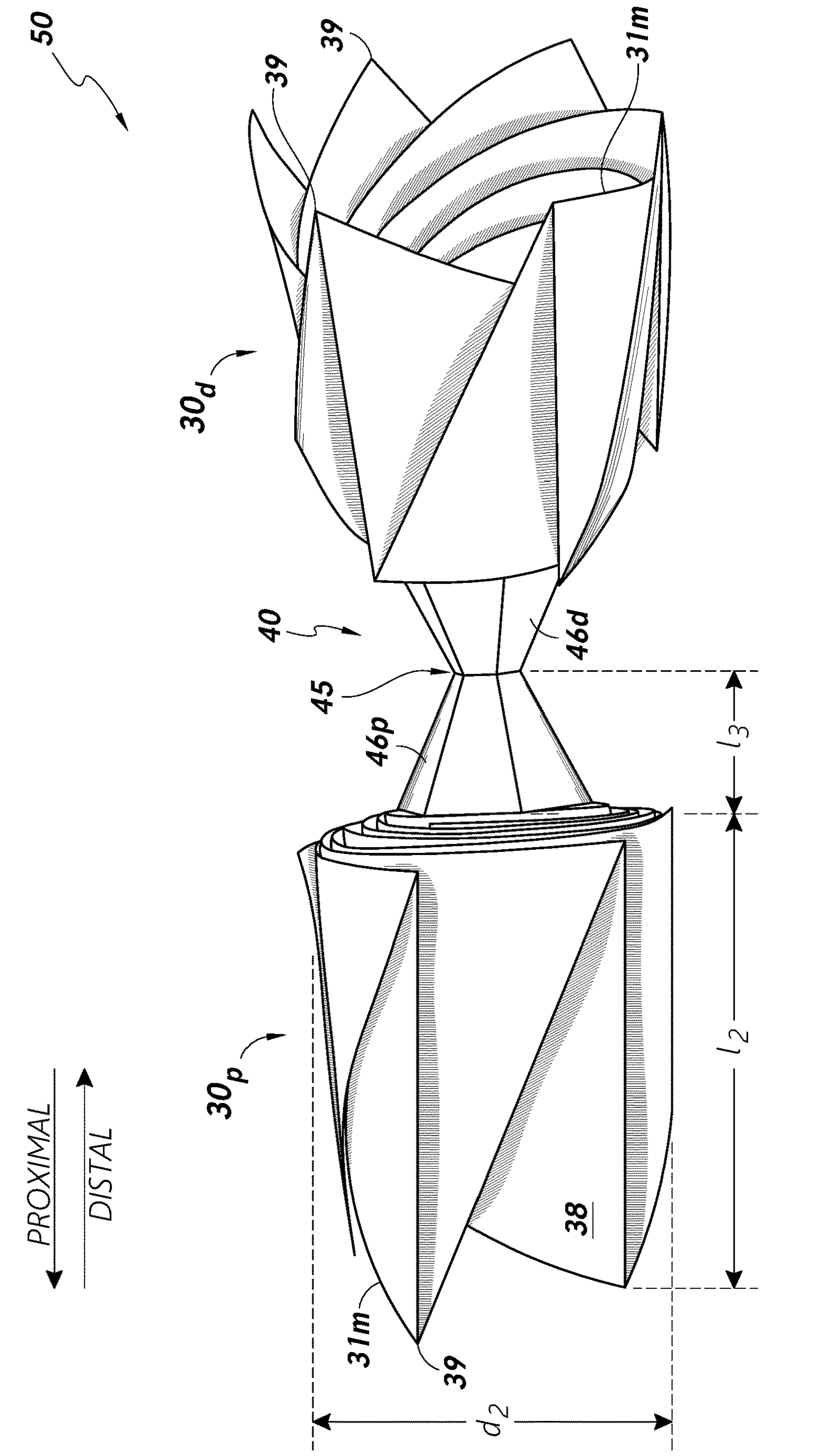

FIGS. 4-1A-4-1C illustrate perspective, side, and axial views of a core 40 of an occluder device in accordance with one or more examples. The core 40 may comprise any suitable or desirable material, such as a plastic or other at least partially rigid material (e.g., Ultem™ or other thermoplastic polyetherimide). The core 40 is advantageously formed of material strong enough to prevent breakage of the core 40, such as at the area of the neck portion 45, during or after implantation.

The core 40 includes a mass or form that includes distal $42_d$ and proximal $42_p$ ends associated with respective axially-narrowing/expanding bulbous, conical, and/or pyramidal (e.g., hexagonal pyramidal) structures 44 that are connected at a relatively narrow neck portion 45. The narrowing/expanding structures 44 can be opposing forms in that they expand, narrow, and/or face in opposite axial directions.

The narrowness of the neck 45 may be designed to accommodate the defect into which the core may be placed/disposed. For example, by having a neck portion 45 that is relatively narrow compared to the distal ends 42 of the core 40, the tissue around the defect may be permitted to enter into the radial space of the core in the area of the neck portion 45. The distal ends 42, which may have associated axial faces, can have any suitable or desirable diameter, such as approximately 7 mm (e.g., about 0.25") or less. Furthermore, the neck portion 45 may have a diameter $d_4$ that is less than the diameter $d_3$. For example, the diameter $d_4$ of the neck portion 45 may be approximately 3 mm (e.g., about 0.125") or less.

In the illustrated example of FIGS. 4-1, the core 40 has an axial cross-section having a polygonal shape, as described above. Therefore, the bulbous pyramidal/conical portions 44 may have flat lateral faces 49 that deflect radially inward towards the neck 45, wherein the expanding/bulbous pyramidal/conical portions 44 may have the same number of sides as the polygonal shape of the distal ends 42 and/or any cross-section of the core 40. The polygonal (e.g., hexagonal) shape of the core 40 may advantageously promote/facilitate folding of wires and/or cloth thereabout, as described in detail herein. The lateral faces 49 can have a truncated triangular shape, wherein the lateral faces 49 and/or expanding/bulbous portions 44 taper towards the axial center of the core 41 where they converge at the neck region 45.

FIGS. 4-2A, 4-2B, and 4-2C show perspective, side, and axial views, respectively, of another example of a core structure 440 that may be implemented in accordance with any of the examples of the present disclosure. In the example of FIGS. 4-2, the core 440 has a curved, hourglass form/shape, as an alternative to the polygonal shape of FIGS. 4-1. Although the bulbous portions 444 are shown as bulging/curved, in some implementations, the core 440 may be implemented with straight, conical sides (albeit circumferentially curved) in the portions 444, such that such portions form frustoconical forms connecting at apices thereof at the neck 445. In the example of FIGS. 4-2, the end and axial cross-sectional shape of the core 440 may be circular or other elliptical, as shown.

Figures 3, 3B, 4, 5:
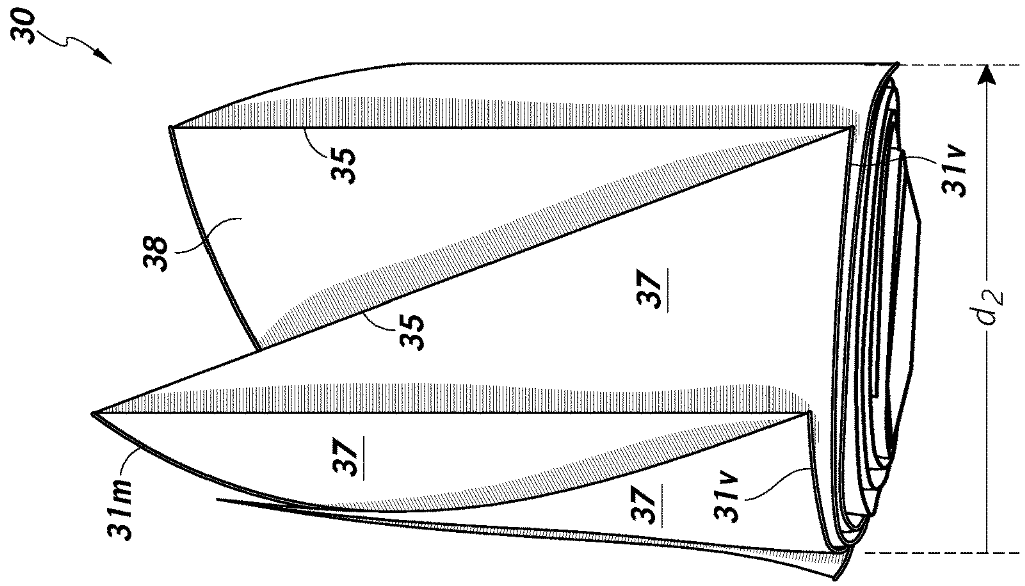
Figures 3, 3A, 4, 5:
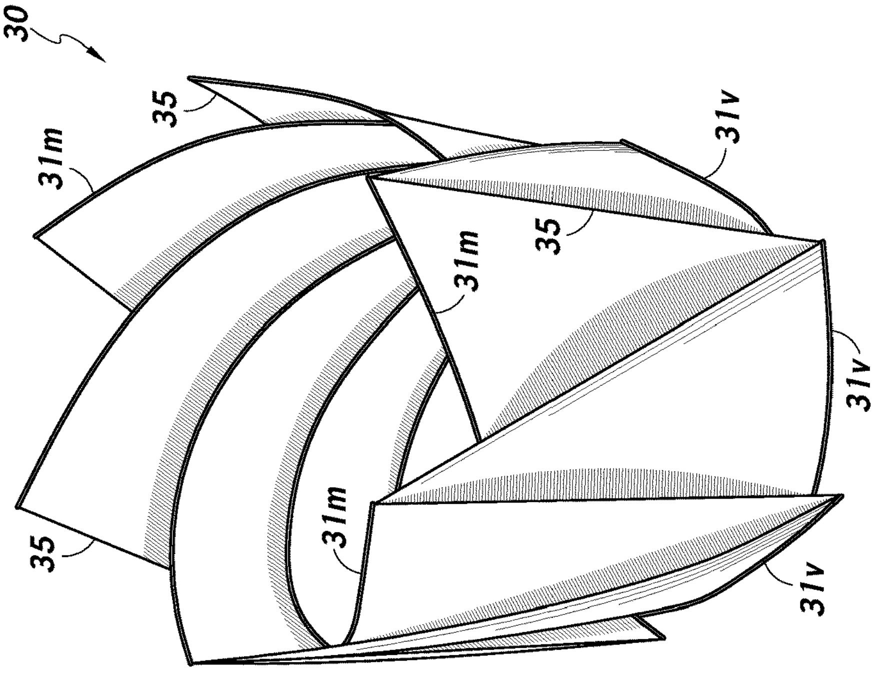

FIG. 5 shows a side perspective view of an occluder device 50 in a delivery configuration in accordance with one or more examples. The occluder device 50 is a dual-cover occluder device as described in connection with various examples disclosed herein. The occluder device 50 includes first $\mathbf{30}_p$ and second $\mathbf{30}_d$ covers coupled to opposite ends of a core structure 40. The covers $\mathbf{30}_p$, $\mathbf{30}_d$ and the core 40 may have any of the features disclosed above in connection with the various other figures presented herein.

In the illustrated delivery configuration of the occluder device 50, the proximal cover $\mathbf{30}_p$ is folded/compressed in a manner such that the peaks 39 associated with the mountain folds $\mathbf{31}_m$ of the cover $\mathbf{30}_p$, as described in detail herein, project in a proximal direction (e.g., in the direction toward the operator when the device 50 is disposed in a delivery system and delivered to target anatomy in accordance with a relevant procedure), whereas the distal cover $\mathbf{30}_d$ is folded such that the peaks 39 associated with the mountain folds $\mathbf{31}_m$ thereof project in a distal direction (e.g., opposite of the proximal direction). That is, in the delivery configuration, the covers $\mathbf{30}_p$, $\mathbf{30}_d$ may advantageously fold and project in opposite directions, and in particular project in opposite directions away from the core 40. Such configuration can prevent the covers 30 from overlapping one another in the delivery configuration. For example, overlapping of the covers 30 may otherwise occur if one or both of the covers 30 compresses inward (as opposed to the outwardly-folding/compressing implementation shown in FIG. 5) in cases in which the compressed/folded covers 30 have a length $l_2$ that is greater than a length $l_3$ of half the axial length of the core 40, as in the illustrated example. The outwardly-folding/compressing configuration of the covers 30 can further advantageously allow for the respective covers to be opened/expanded in a manner as to produce a convexity in the respective covers in the direction of the center neck region 45 of the core 40. That is, in certain expanded and/or partially-expanded configurations, the respective covers 30 may form dish-like forms having apices facing one another to thereby accommodate a tissue/septal wall that narrows radially toward the axis/center of the core 40.

The compressed delivery configuration shown in FIG. 5 can allow for a desirable ratio of diametrical delivery profile $d_2$ relative to the expanded cover diameter $d_1$ (see, e.g., FIG. 2) that is suitable for placement in a delivery catheter in the delivery configuration, yet allows for large enough expansion of the respective covers 30 to cover areas of tissue that are substantially larger than the compressed delivery profile $d_2$ of the device 50. The compression ratio of the device 50 can be enabled by the use of independent wires 31 in the respective covers 30, as described in detail above, which may allow for relatively tight wrapping of the wires 31 and folding of the covering 38 between the wires 31 in a relatively flat and tight configuration around the core 40 in the cylindrical form shown. Generally, the diameter $d_3$ (see, e.g., FIG. 4-1B) of the core 40 may limit how small the profile of the device 50 can be in the delivery configuration shown in FIG. 5. Therefore, it may be desirable to construct the core 40 with a diameter that is sufficiently large to allow for securing thereto of the wires of the respective covers 30, while minimizing the diameter for the purpose of reducing the delivery profile of the device. In some examples, the fully-compressed diameter $d_2$ of the covers 30 is about 6 mm or less, whereas in the expanded configuration, the covers 30 may be configured to assume an expanded diameter of up to about 30 mm, or more. That is, the ratio of expanded diameter to compressed diameter may be as much as five or more to one, or greater.

With both of the covers 30 in the fully compressed configuration shown in FIG. 5, the covers 30 form dual open cylinders that are open axially-outward. Therefore, the covers 30 form open cylinders that are open in opposite directions, as shown.

Figure 6:
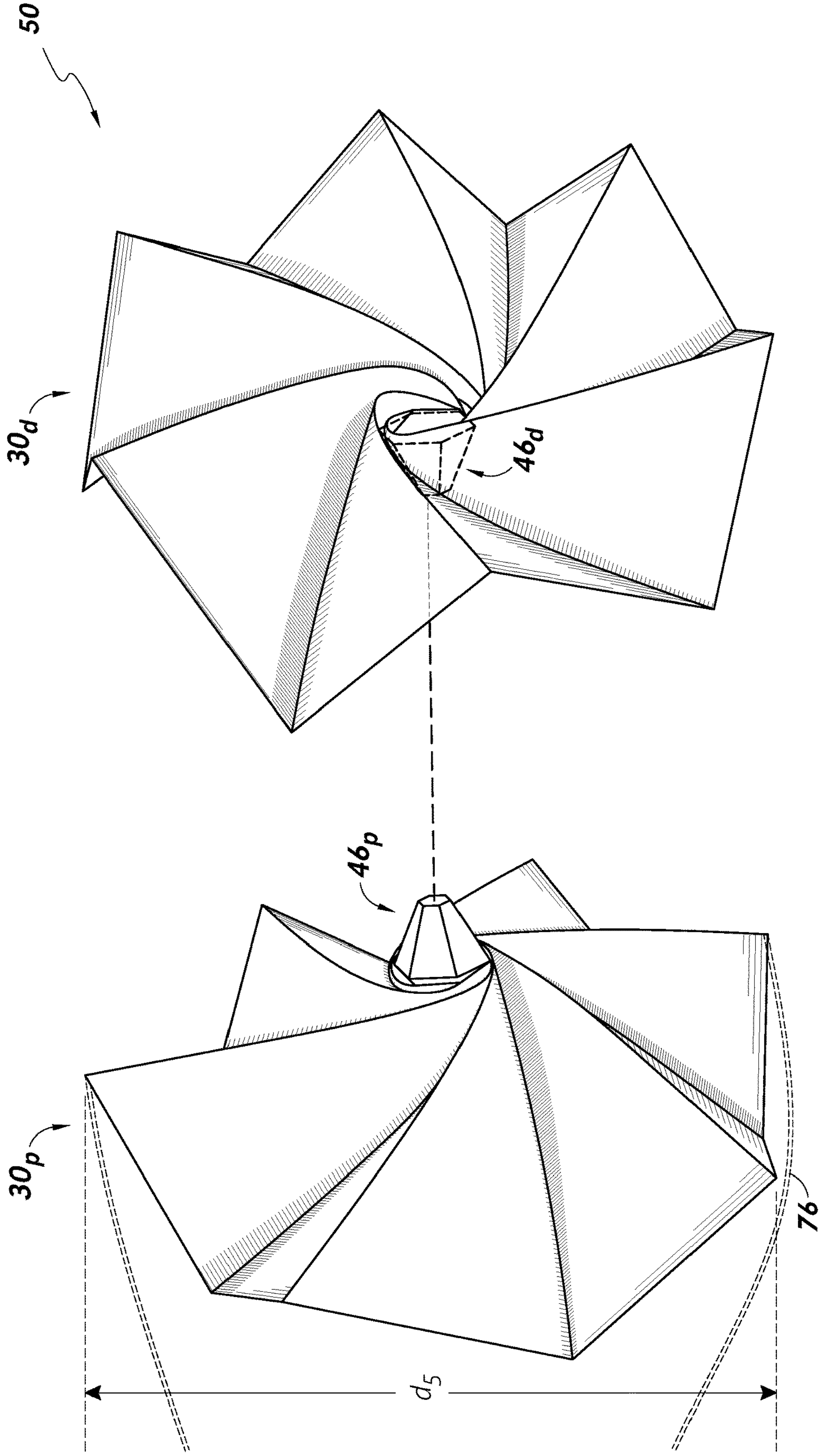
FIG. 6 shows an exploded perspective view of the occluder device of FIG. 5 in a partially-expanded configuration in accordance with one or more examples.

FIG. 6 shows an exploded perspective view of the occluder device 50 of FIG. 5 in a partially-expanded configuration in accordance with one or more examples. In the partially-expanded state/configuration shown in FIG. 6, both of the covers $\mathbf{30}_p$, $\mathbf{30}_d$ are shown as partially-expanded. However, it should be understood that during implantation, the respective covers $\mathbf{30}_d$, $\mathbf{30}_p$ may be expanded at different times, such that they may be at different states/stages of expansion at any given time. The image of FIG. 6 is shown as an exploded view to allow for visualization of the core 40, wherein core portion $\mathbf{46}_p$ is visible, whereas core portion $\mathbf{46}_d$ is visually covered due to the perspective of the view of FIG. 6.

As described above, intermediate expansion of the cover(s) 30 can allow for different sizes and shapes/contours of the cover(s) with respect to the expanded diameter thereof; different states of expansion of the covers can produce different diameters, shapes, contours, and/or topology of the covers in the various states of expansion. In some implementations, it may be desirable to deploy/implant the device 50 such that at least one of the covers 30 is in an intermediate state of expansion. However, such intermediate expansion states can present certain contours/angles of the various portions/segments of the covers that can lead to risk of pooling/stagnation of blood and/or embolism formation due to blood trapping. However, depending on the particular anatomy in which the device 50 is implanted, the relevant pressure levels may serve to prevent embolism formation, and therefore intermediate-expansion deployment may be tenable or suitable in some cases.

Figure 7A:
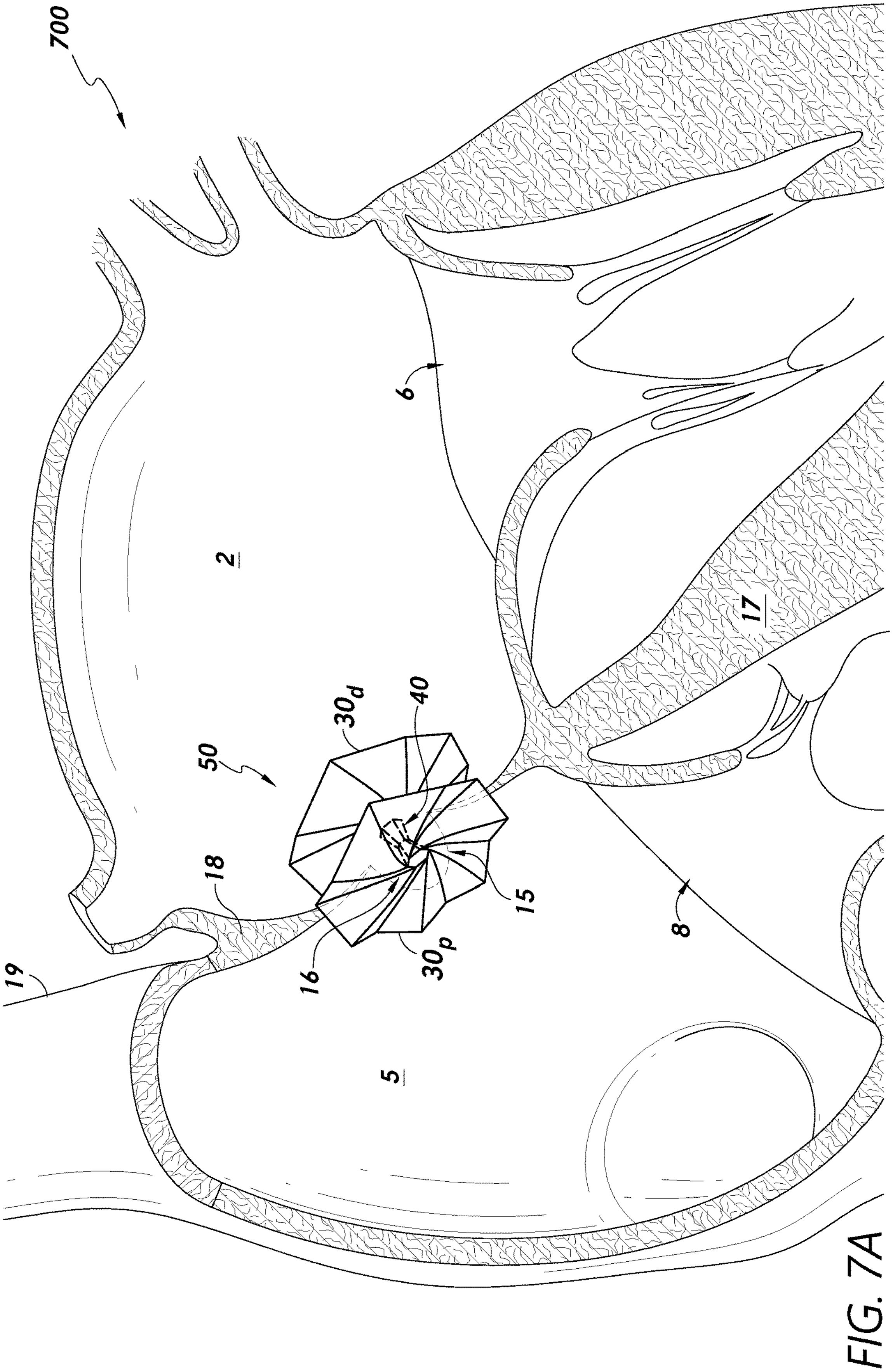
FIGS. 7A and 7B illustrate an occluder device deployed in a septal defect in accordance with one or more examples.
Figure 7B:
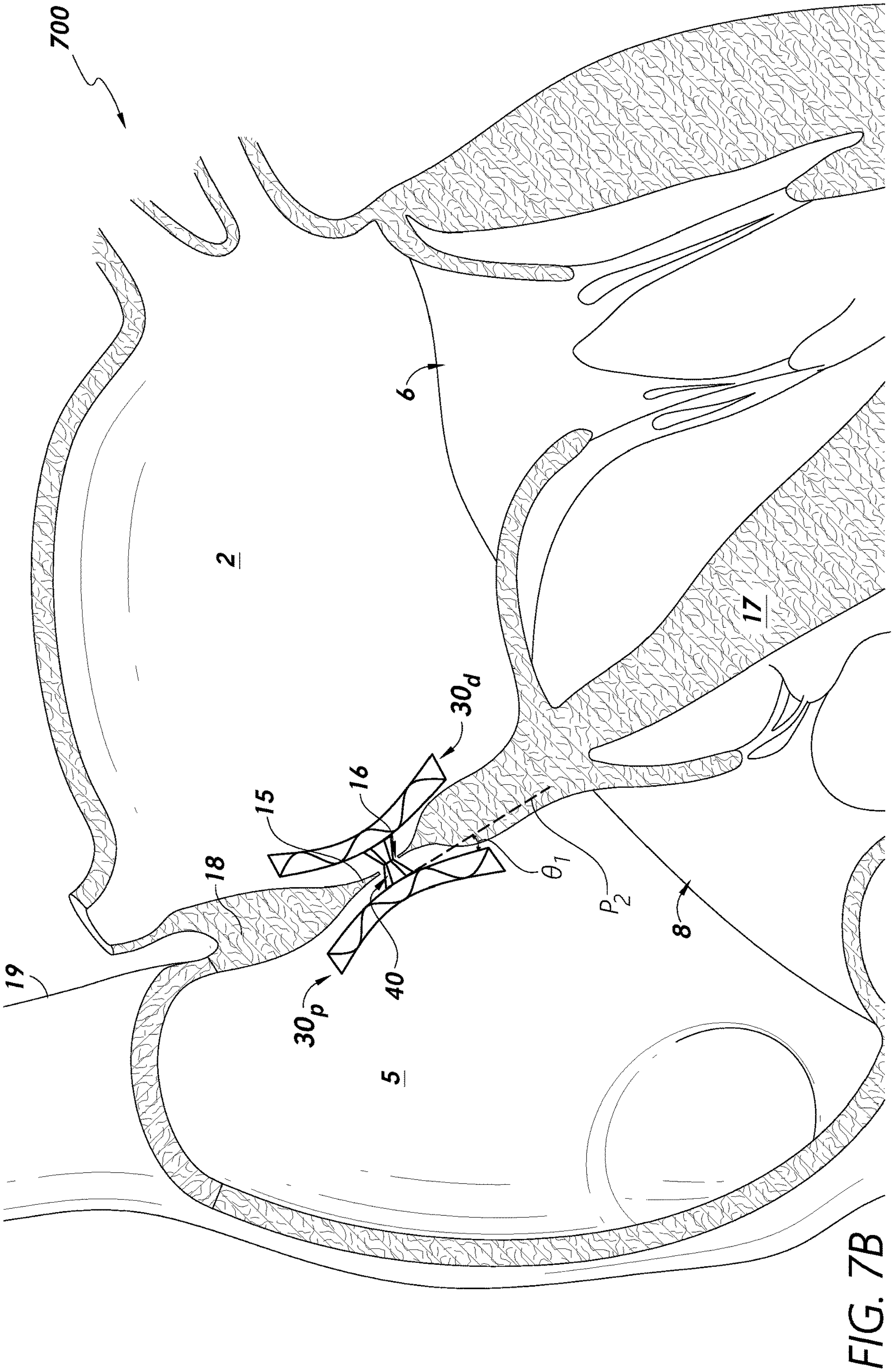

FIGS. 7A and 7B illustrate an occluder device 50 deployed in a septal defect 16 in accordance with one or more examples. In the implanted configuration, the covers $\mathbf{30}_p$, $\mathbf{30}_d$ may be in substantially flat (e.g., fully-expanded) configurations, as in FIG. 2, or may be in at least partially compressed/folded configuration(s), as shown in FIGS. 7A and 7B. As shown, when implanted, the core 40 may traverse the defect 16 (which is covered by the defect cover $\mathbf{30}_p$ in the illustrated image, but visible in dashed form), such that the distal cover $\mathbf{30}_d$ is deployed/disposed on one side (e.g., left atrium side) of the tissue wall 18 (e.g., atrial septum), whereas the proximal cover $\mathbf{30}_p$ is deployed/disposed on an opposite side (e.g., right atrium side) of the tissue wall 18.

In some examples, the defect covers 30 comprise twelve (or other number) thin, flexible nitinol wires arranged in a spiral and connected to a hexagonally-shaped core 40. In some examples, the sides of the covers touching the tissue wall 18 are covered in a biocompatible cloth as scaffolding for tissue growth and to provide sealing functionality. The spiral, flat design of the disc-type covers 30 can allow the device to furl down to a much smaller profile relative to the structure's expanded size. With memory metal shape memory, the covers can be configured to self-expand into a relatively flatter disc shape once released from the delivery catheter.

The partially-expanded/folded state shown in FIGS. 7A and 7B can produce a configuration of one or more of the covers 30$_p$, 30$_d$ wherein one or more sets of wires (e.g., valley fold wires and/or mountain fold wires) thereof are deflected axially away from the core 40 to some degree, as best seen in the close-up side view of FIG. 7B. Such configuration may deflect the covers away from the plane $P_2$ of the tissue wall 18 in a manner that may be better suited to accommodate the topology of the tissue wall 18 on one or more sides thereof. For example, with respect to defects in the atrial septum 18 in the area of the fossa ovalis 15, the fossa ovalis 15 and atrial septum 18 may generally gradually thin-out moving from the outer portions of the septal wall inward towards the center of the fossa ovalis 15, thereby producing a concavity on one or both sides of the tissue wall 18. Therefore, in view of such concavity, flat occlusion covers can result in undesirable pockets or gaps between the occluder and the tissue wall in which blood may pool/stagnate. As shown in FIG. 7B, the inward convexity of the covers 30, which may result from expanding the covers 30 to a partially-expanded state in which the mountain and valley fold wires, respectively, do not lie in the same plane or in a plane parallel to the plane $P_2$ of the tissue wall or an axial plane of the device 50, can seat more closely against the anatomy compared to completely flat covers.

The ability to expand the covers 30 to various intermediate states of expansion can allow for configurations of the covers having varying diameters. That is, a fully expanded configuration of a defect cover in accordance with aspects of the present disclosure may have a greater diameter than a configuration of the same cover in a partially-expanded state, which may have a relatively smaller diameter. Therefore, occluder devices in accordance with aspects of the present disclosure may be suitable for implantation in patients having varying anatomies. For example, an occluder device in accordance with the present disclosure may be configurable to multiple diametrical sizes, wherein a particular size/expansion state may be implemented to fit/suit the particular anatomy of the patient. That is, the angle $\theta_1$ of the concavity of one or more of the covers 30 can provide a convex tissue-facing surface that allows the cover to sit relatively deeper in the fossa ovalis and/or defect associated with the tissue wall 18.

Control of the degree of expansion of the covers 30 can be controlled using suture tensioning or other mechanism to hold a cover and/or one or more wires associated therewith in a desired state of expansion. For example, in some implementations, one or more sutures 76 (see FIG. 6) may be coupled to one or more of the radially-expanding wires 31 of a cover of an occluder device 50, wherein such suture(s) is/are configured to be pulled or adjusted to hold a desired position or tension in the wires associated with a desired expansion configuration. In some examples, one or more clasps, locks, clamps, or other locking means or mechanism may be associated with the device 50 and/or associated delivery system for locking the suture tensioning at the desired expansion state to produce the desired size of the cover(s) 30 for deployment. In some implementations, such locking sutures may be cut or otherwise removed (e.g., un-looped) such that the suture tensioning is not permanent and/or not retained in the device 50 after deployment/implantation.

Figure 8:
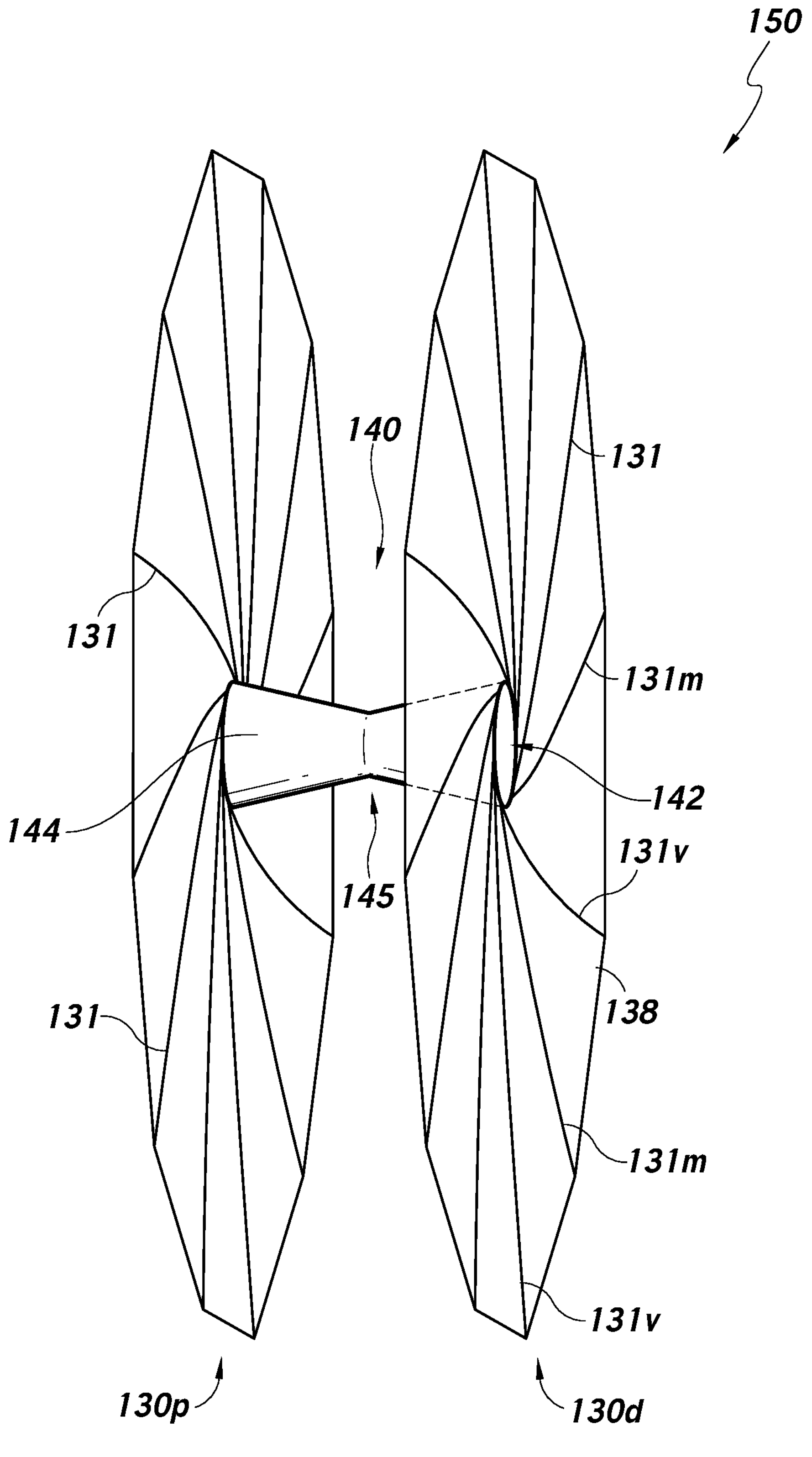
FIG. 8 is a perspective view of an occluder device in accordance with one or more examples.

FIG. 8 is a perspective view of an occluder device 150 in accordance with one or more examples. The occluder device 150 of FIG. 8 can include any of the features of any of the other occluder devices disclosed herein. For example, the occluder device 150 includes a core 140 connected at opposite ends to respective covers 130$_p$, 130$_d$. Each of the covers 130 includes alternating mountain 131$_m$ and valley 131 fold wires about which the covering 138 can fold as the wires are wrapped circumferentially around the core 140 to assume more compressed configurations, such as for transport and/or to fit the particular anatomy against which the respective cover is positioned/disposed. In the example of FIG. 8, the occluder device 150 includes a core 140 having curved geometry, rather than the polygonal geometry shown in certain other figures. Therefore, the core 140 may have a form resembling dual frustoconical shapes joined at a relatively narrow neck portion 145.

Figure 9:
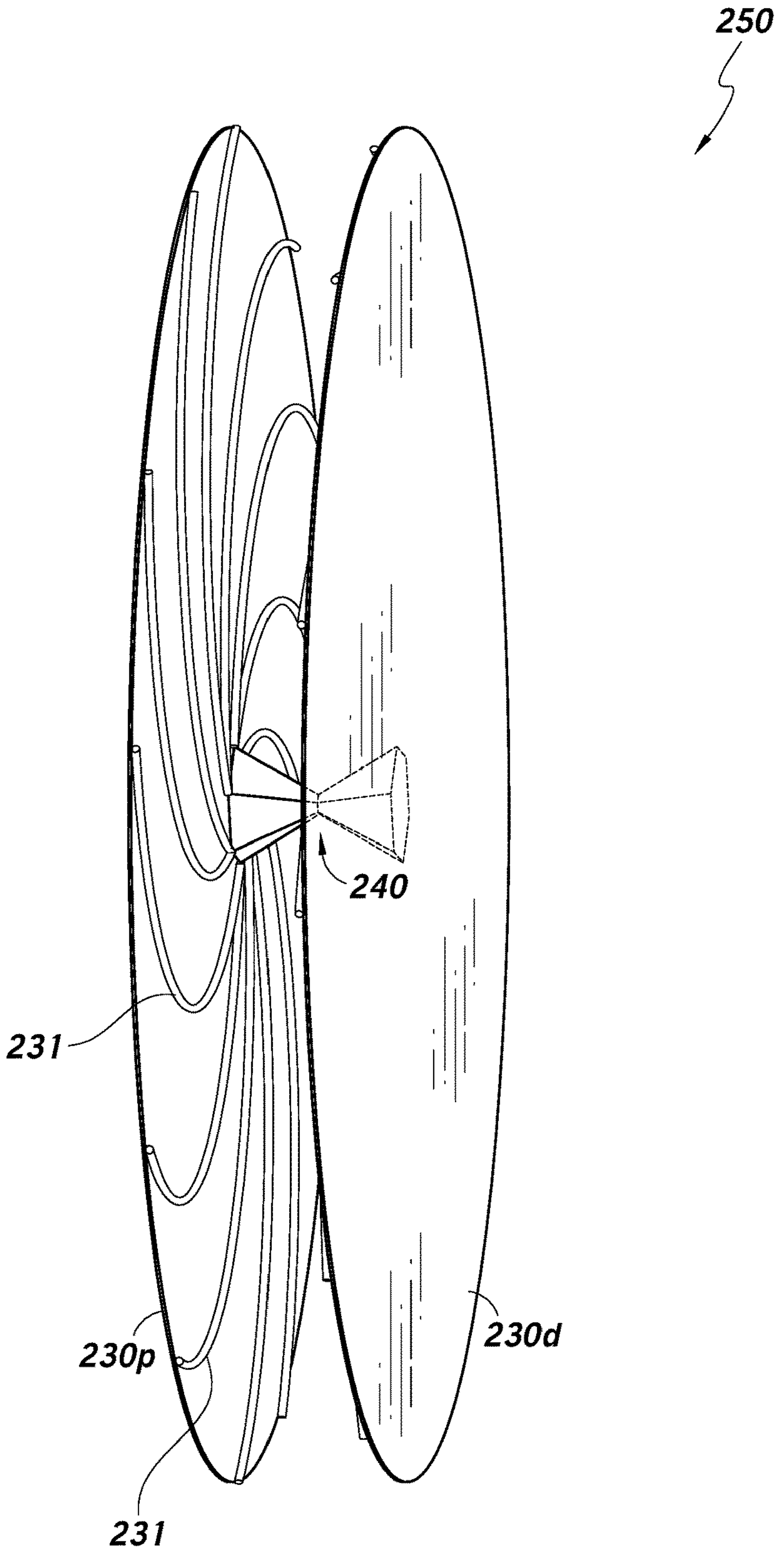
FIG. 9 is a perspective view of an occluder device in accordance with one or more examples.
Figures 1, 10:
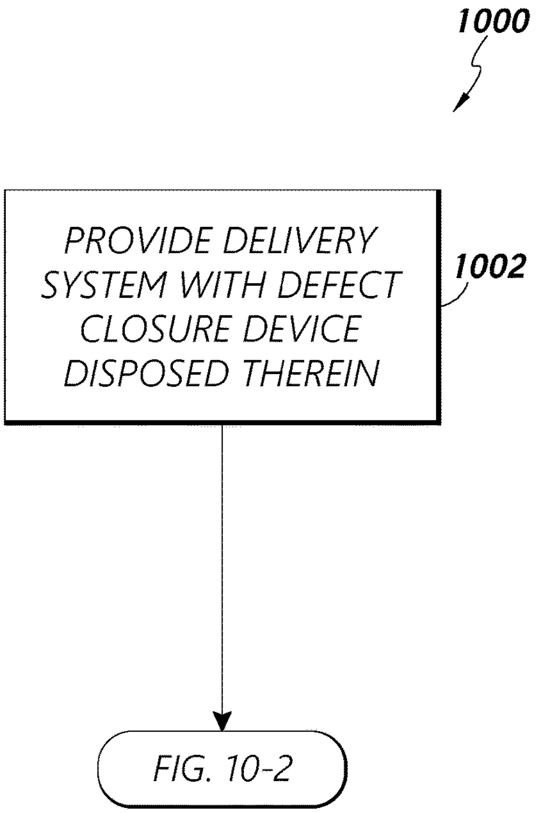

FIG. 9 is a perspective view of an occluder device 250 in accordance with one or more examples. In the example of FIG. 9, the occluder device 250 may be similar in certain respects to certain other occluder devices disclosed herein. For example, the occluder device 250 may include a plurality of covers 230, which are coupled to a plurality of wires 231, each of which may be coupled at proximal portions thereof to a core 240 connected between the covers 230$_p$, 230$_d$. In the example shown, the fold wires 231, which may comprise alternating mountain and valley fold wires as with other examples shown and disclosed herein, may have a greater degree of curvature compared to the fold wires associated with other covers disclosed herein. For example, whereas the fold wires 31 in the cover example shown in FIG. 2 may have only slight curvature, such curvature being in a circumferential direction with respect to the axis of the cover 30, the curvature of the wires 231 in FIG. 9 can be greater. For example, for a given fold wire 231, in some examples, the radius of curvature thereof is less than the length of the wire, or less than two times the length of the wire in some examples. The more exaggerated curvature of the fold wires 231 in the occluder device 250 can facilitate wrapping of the wires 231 around the axis of the core 240 in the delivery configuration. However, in some cases, a tighter cylindrical form may be achievable with wires having relatively less curvature, such as in the example shown in FIG. 2.

FIGS. 10-1, 10-2, and 10-3 provide a flow diagram illustrating a process 1000 for implanting an occluder device 50 in accordance with one or more examples. FIGS. 11-1, 11-2, and 11-3 provide images of cardiac anatomy and certain devices/systems corresponding to operations of the process 1000 of FIGS. 10-1, 10-2, and 10-3 in accordance with one or more examples.

Figures 1, 11:
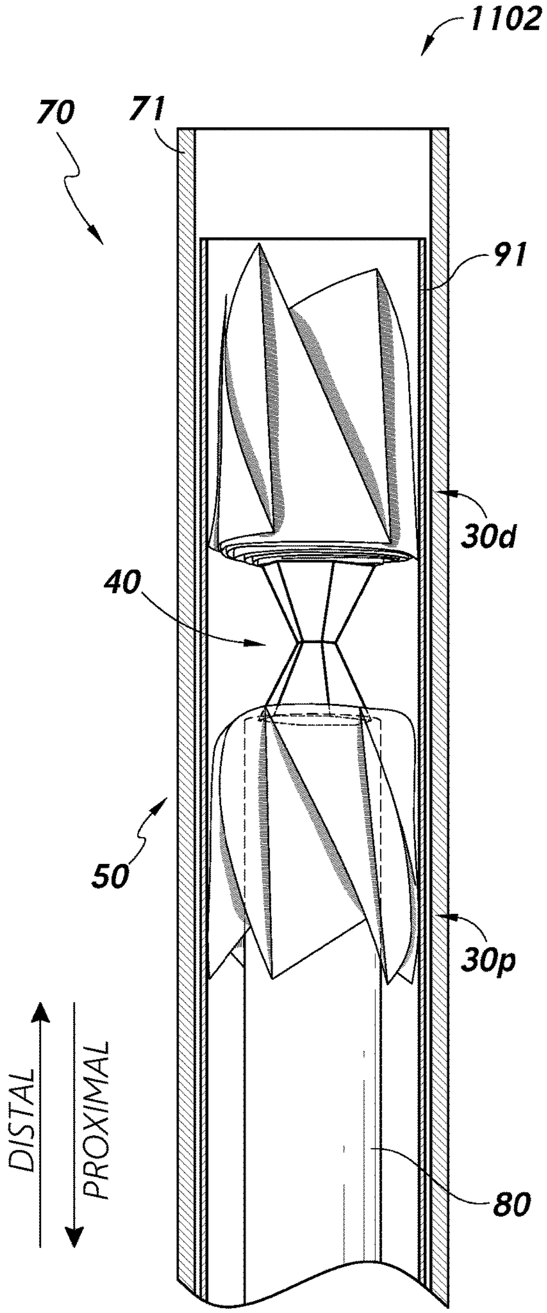
Figures 2, 10:
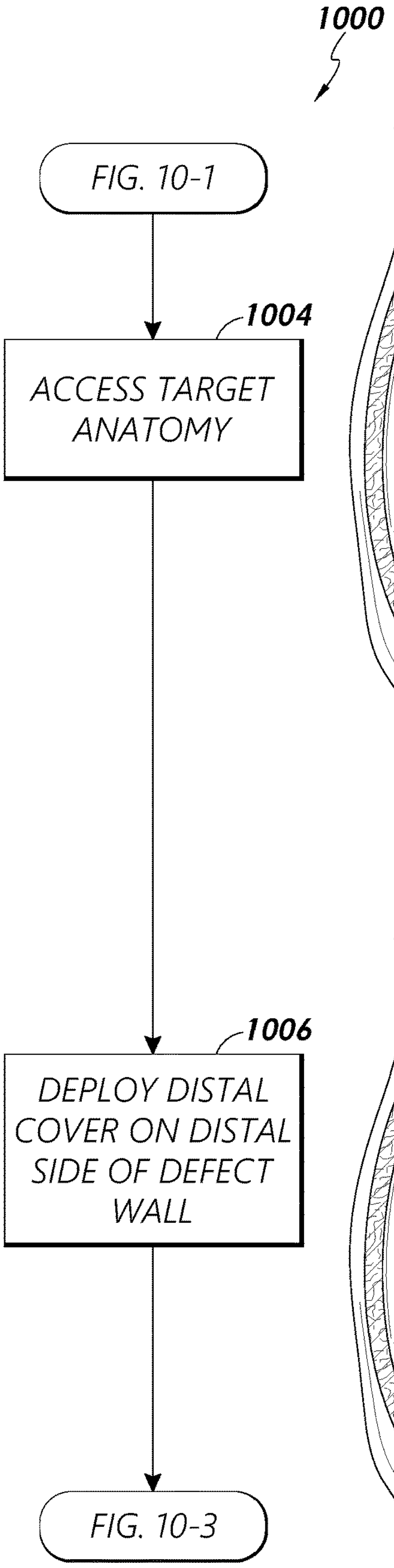
Figures 2, 11:
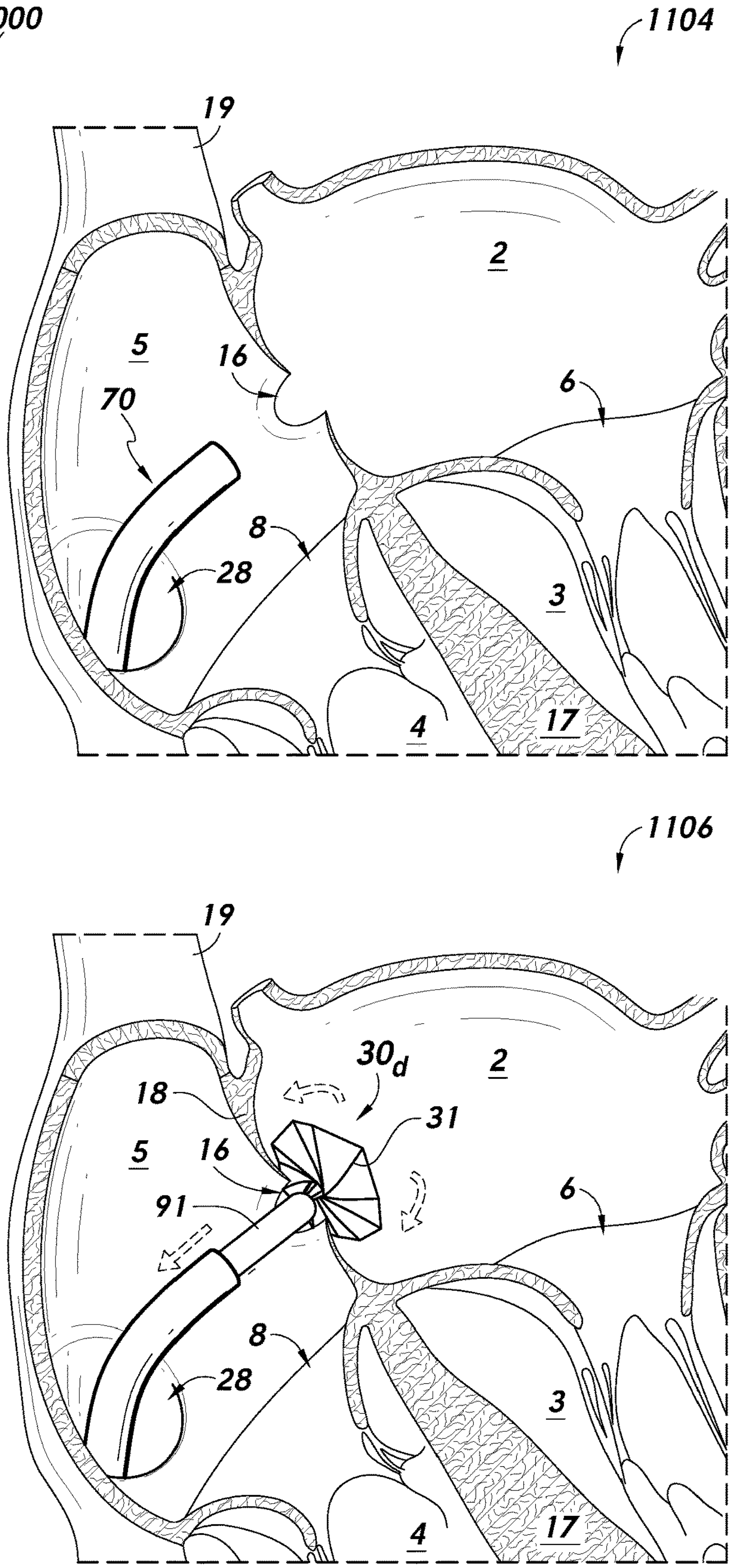
Figures 3, 10:
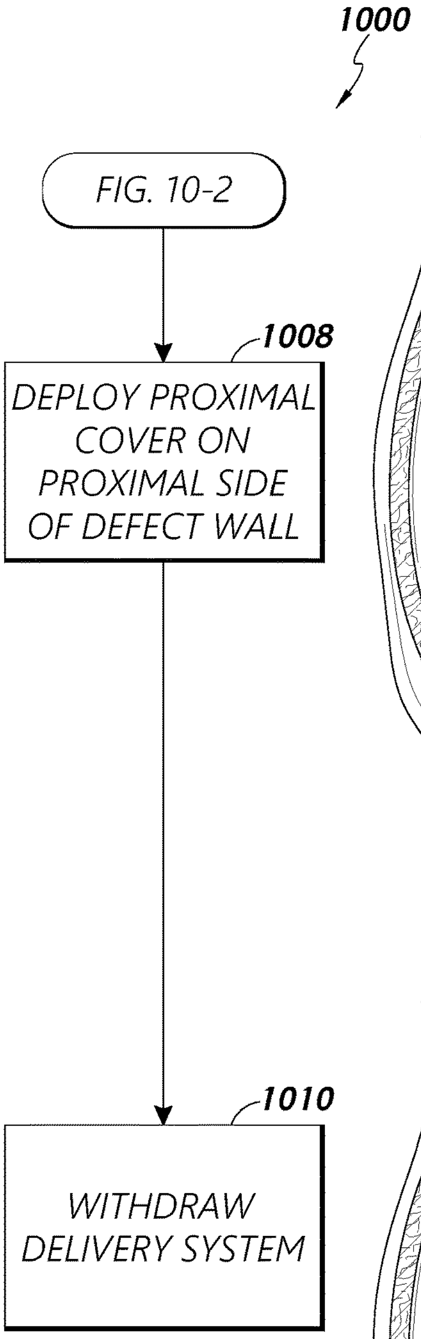
Figures 3, 11:
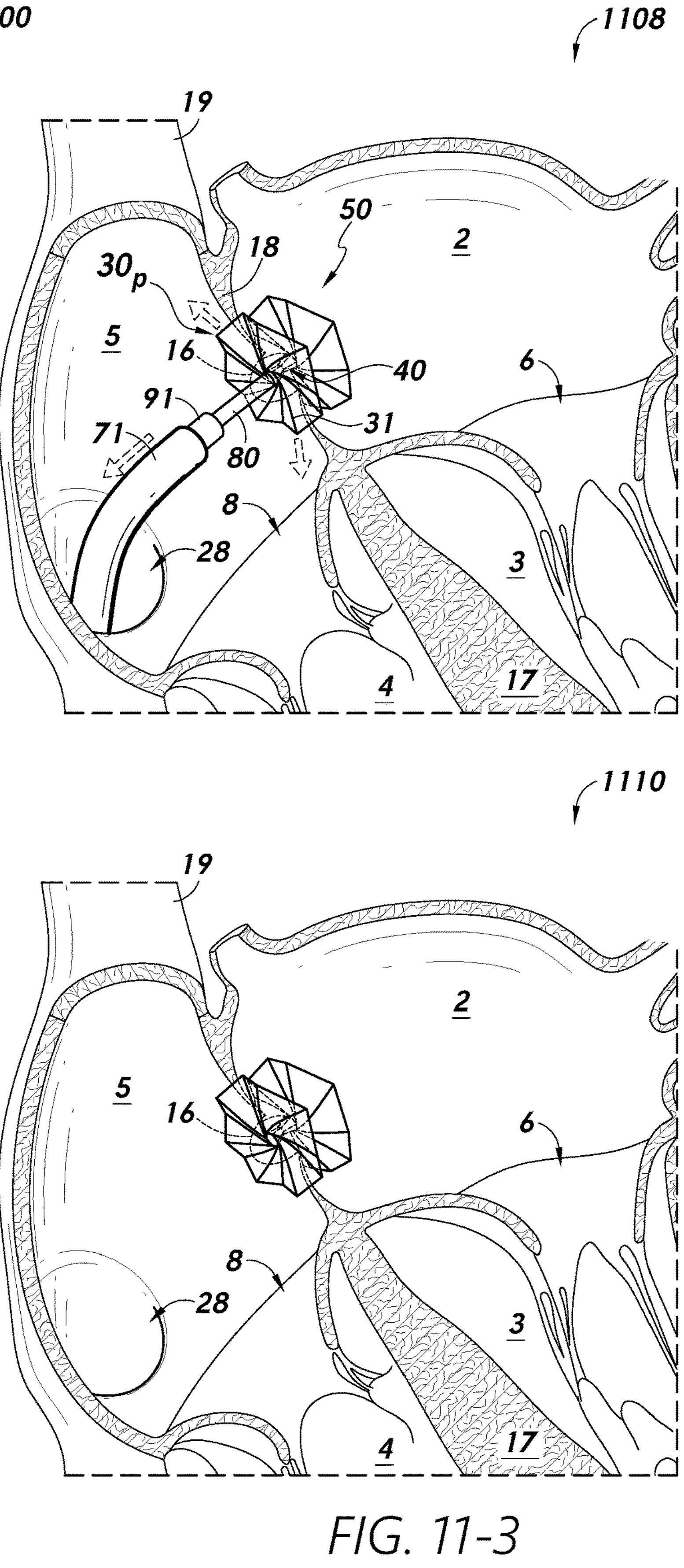

At block 1002, the process 1000 involves providing a delivery system 70 with an occluder device 50 disposed therein in a delivery configuration. Image 1102 of FIG. 11-1 shows a partial cross-sectional view of the delivery system 70 and occluder device 50 in accordance with one or more examples of the present disclosure. The image 1102 shows the occluder 50 disposed within an outer sheath 71 of the delivery system 70. Although a particular example of a delivery system is shown in FIG. 11-1, it should be understood that occluder devices in accordance with aspects of the present disclosure may be delivered and/or implanted using any suitable or desirable delivery system and/or delivery system components.

With respect to implantation processes for dual-cover occluder devices in accordance with aspects of the present disclosure, generally, one cover may first be deployed in the left atrium in front of the atrial defect in the left atrial chamber, after which the delivery catheter is withdrawn through the septal defect and the second cover is placed on the right atrial side of the defect/wall. Both covers advantageously can have at least one diameter dimension, or an area, that is larger than that of the defect opening in order to fully cover the opening. The two covers of the dual-cover device can face in opposite directions, as shown in image 1102, or may both face in the same direction.

The illustrated delivery system 70 includes an inner sheath/catheter 91, which may be disposed at least partially within the outer sheath 71 during one or more periods of the process 1000. In some examples, the delivery system 70 may be configured such that a guidewire may be disposed at least partially therein. For example, the guidewire may run in the area of an axis of the sheath 71 and/or inner catheter 91, such as within the inner catheter 91. The delivery system 70 may be configured to be advanced over the guidewire to guide the delivery system 70 to a target implantation site.

The outer sheath 71 may be used to transport the occluder device 50 to the target implantation site. That is, the occluder device 50 may be advanced to the target implantation site at least partially within a lumen of the outer sheath 71 and/or inner sheath 91, such that the occluder device 50 is held and/or secured at least partially within a distal portion of the outer sheath 71 and/or inner sheath 91. The terms "catheter" and "sheath" are used herein according to their broad and ordinary meanings and may refer to any type of tube suitable for insertion in the body. "Catheter" and "sheath" may be used substantially interchangeably is some contexts herein. Similarly, the terms "catheter," "tube," "shaft" (e.g., inner/outer shaft), "sheath," "delivery sheath," "steerable sheath," and/or "steerable catheter" are used herein according to their plain and ordinary meanings and can refer or apply generally to any type of elongate and/or tubular delivery devices.

At block 1004, the process 1000 involves accessing a target site/anatomy with the delivery system 70. For example, such access may be made through a transcatheter access path, as described herein. In some examples, the target anatomy is a chamber of the heart of the patient, for example. In some implementations, access to the target implantation site may be facilitated using a guidewire. For example, a guidewire may be disposed within the delivery system 70, such as within the outer sheath 71. In some implementations, the guidewire may pass through the pusher 80 and/or the occluder device 50. For example, the core 40 of the occluder device 50 can have an axial hole through which a guidewire can pass.

At block 1006, the process 1000 involves deploying the distal cover $\mathbf{30}_d$ from the inner sheath 91 on a distal (e.g., left atrial) side of the tissue wall 18. For example, the tissue wall 18 may be an atrial septum having a defect 16 formed therein. Deploying the distal cover $\mathbf{30}_d$ from the inner sheath 91 may be performed after first deploying the inner sheath 91 from the outer sheath 71, as shown in image 1106. Deploying the distal cover 30*d* may involve proximally pulling back the inner sheath 91 and/or distally pushing the occluder device 50, such as by distally pushing the pusher/catheter 80 to move the core 40 and/or other aspect(s) of the device 50 relative to one or more components of the delivery system 70 (e.g., the inner catheter 91). Relative movement of the inner sheath 91 proximally with respect to the implant device 50 can cause the cover $\mathbf{30}_d$ to be deployed from the inner sheath 91, wherein upon deployment from the inner sheath 91, the cover $\mathbf{30}_d$ and/or wires 31 thereof may have shape memory that causes the cover to expand outward radially to form a disc and/or dish-type shape/form configured to cover over the defect 16.

At block 1008, the process 1000 involves deploying the proximal cover $\mathbf{30}_p$ on the proximal/opposite side of the defect wall 18. Such deployment of the cover $\mathbf{30}_p$ may be implemented by further withdrawing proximally the inner sheath 91 relative to the implant device 50 and/or distally pushing the implant device 50 relative to the inner sheath 91. For example, a pusher or catheter 80 may be coupled to the core 40 of the implant device 50 during one or more periods of the implantation process, such that distally moving or applying pressure to the pusher/catheter 80 can cause the implant device 50 to be distally moved accordingly. The pusher/catheter 80 may be coupled to a proximal portion of the core 40 and/or any other component(s) of the device 50 using any suitable or desirable means or mechanism. For example, the pusher 80 may be coupled to the core 40 using one or more sutures, which may be looped through one or more hook or hoop features of the core 40 and/or other component(s) of the device 50, wherein such suture(s) may be withdrawn from such coupling to thereby release the pusher 80, and therefore the delivery system 70, from the device 50 after placement thereof.

When the cover 30, is deployed from and/or moved out of the inner sheath 91 on the proximal (e.g., right atrial) side of the tissue wall 18, the shape memory of the cover 30*p* and/or wires 31 thereof may cause the cover 30*p* to expand radially outwardly, as described in detail herein.

In some implementations, the process 1000 may involve controlling a degree of expansion of one or more of the covers 30, such as through the use of one or more tensioning sutures coupled to one or more of the wires or other components of a cover, wherein such suture(s) may be configured to permanently hold a desired and/or locked tension therein, thereby retaining one or more of the covers in a desired state of expansion, or the suture(s) may be utilized only temporarily during implantation and withdrawn and/or disengage from the device 50 after/during deployment. One or more of the covers 30 may advantageously be deployed to a partially-expanded, rather than fully-expanded, state in some implementations in order to provide a custom fit to the target anatomy (e.g., tissue wall 18), and/or to better fit within the topology (e.g., concavity) of the tissue wall 18. For example, the covers 30 may be expanded to form a concavo-convex disc form, which may have certain radial ridges/pleats therein formed by the folds around the respective radial folding wires 31. The convex side of such forms may be placed against the respective sides of the tissue wall 18 in a manner such that the tapering of such covers lies desirably against the thinning/concave portions of the wall 18.

At block 1010, process 1000 involves withdrawing the delivery system, leaving the implant device 50 in place to provide occlusion functionality with respect to the defect 16. That is, the implanted device 50 may prevent shunting of blood between the atria 2, 5, such as may occur predominantly from the left atrium 2 to the right atrium 5 due to the pressure gradient that may be present in certain periods of the cardiac cycle.

Figure 12:
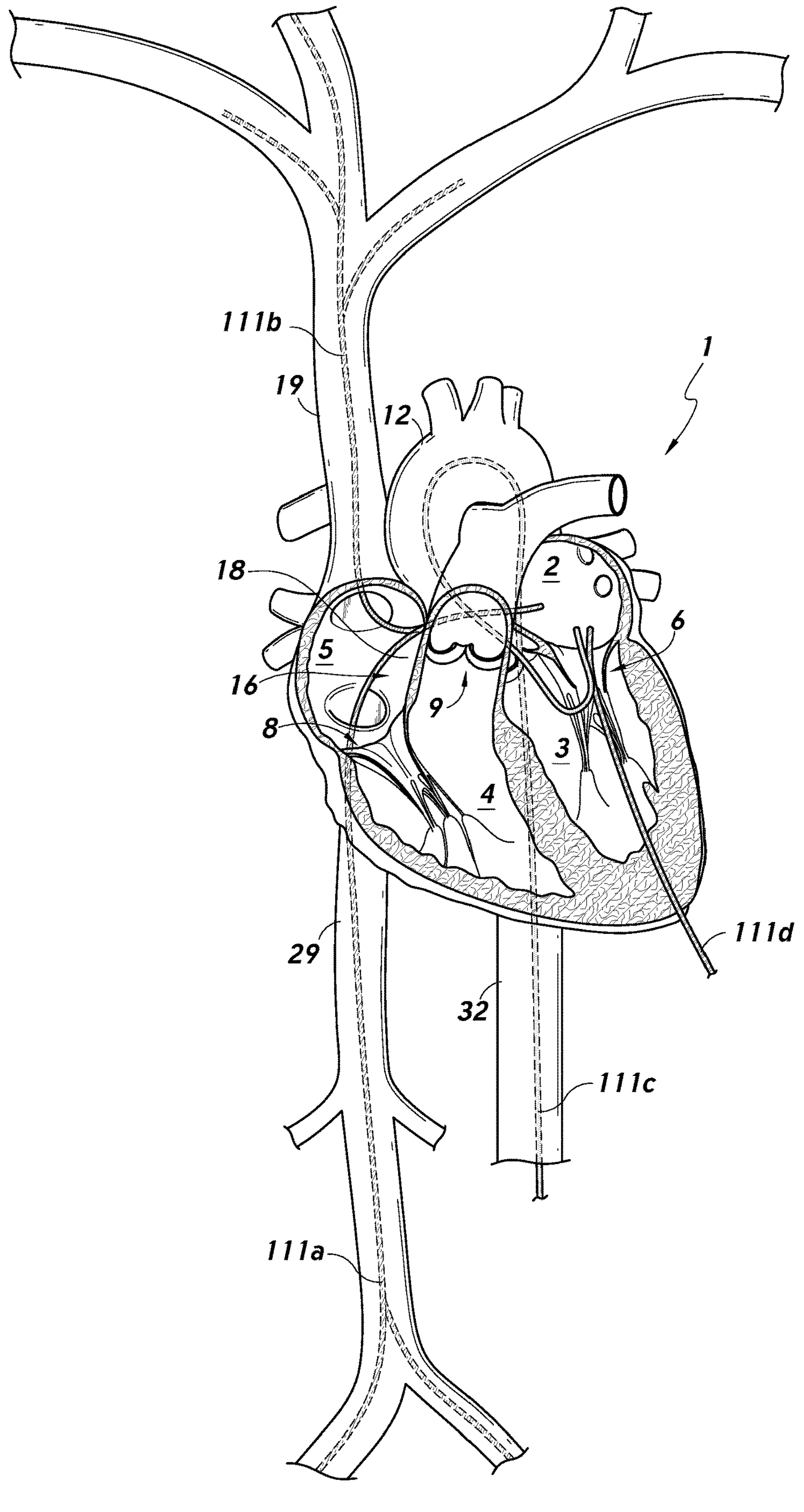
FIG. 12 is a cutaway view of a human heart and associated vasculature showing certain catheter access paths for occluder device implantation procedures in accordance with one or more examples.

FIG. 12 is a cutaway view of a human heart 1 and associated vasculature showing certain catheter access paths for occluder device implantation procedures in accordance with one or more examples. FIG. 12 shows various catheters 111 that may be used to implant sensor devices in accordance with aspects of the present disclosure. The catheters 111 can advantageously be steerable and relatively small in cross-sectional profile to allow for traversal of the various blood vessels and chambers through which they may be advanced en route to, for example, the right atrium 5, left atrium 2 or other anatomy or chamber. Catheter access to the right atrium 5, coronary sinus 16, or left atrium 2 in accordance with certain transcatheter solutions may be made via the inferior vena cava 29 (as shown by the catheter 111*a*) or the superior vena cava 19 (as shown by the catheter 111*b*). Further access to the left atrium 2 may involve crossing the atrial septum 18 (e.g., in the area at or near the fossa ovalis).

Although access to the atrial septum 18 is illustrated and described in connection with certain examples as being via the right atrium 50 and/or vena cavae, such as through a transfemoral or other transcatheter procedure, other access paths/methods may be implemented in accordance with examples of the present disclosure. For example, alternatives to transseptal access can include transaortic access, wherein a delivery catheter 111*c* is passed through the descending aorta 32, aortic arch 12, ascending aorta, and aortic valve 7, and into the left atrium 2 through the mitral valve 6. Alternatively, transapical access may be implemented to access the target anatomy, as shown by delivery catheter 111*d*.

Additional Description of Examples

Provided below is a list of examples, each of which may include aspects of any of the other examples disclosed herein. Furthermore, aspects of any example described above may be implemented in any of the numbered examples provided below.

Example 1: An occluder device comprising a core form having first and second axial ends, a first plurality of wires emanating radially from the first axial end of the core form, the first plurality of wires being configured to circumferentially wrap around an axis of the core form, a first covering coupled to at least one of the first plurality of wires or the first axial end of the core form, a second plurality of wires emanating radially from the second axial end of the core form, the second plurality of wires being configured to circumferentially wrap around the axis of the core form, and a second covering coupled to at least one of the second plurality of wires or the second axial end of the core form.

Example 2: The occluder device of any example herein, in particular example 1, wherein the first covering is configured to fold at each of the first plurality of wires to form radial pleats.

Example 3: The occluder device of any example herein, in particular example 2, wherein the first plurality of wires includes first and second alternating sets of wires, the first set of wires is configured to wrap circumferentially around the axis of the core form at a first angle with respect to an axial plane associated with the core form, and the second set of wires is configured to wrap circumferentially around the axis of the core form at a second angle with respect to the axial plane, the second angle being greater than the first angle.

Example 4: The occluder device of any example herein, in particular example 3, wherein the first set of wires is disposed on a first side of the first covering, and the second set of wires is disposed on a second side of the first covering that is opposite the first side.

Example 5: The occluder device of any example herein, in particular examples 1-4, wherein the core form has a polygonal axial cross section at the first axial end.

Example 6: The occluder device of any example herein, in particular example 5, wherein the core form has a hexagonal axial cross section at the first axial end.

Example 7: The occluder device of any example herein, in particular example 5, wherein the first plurality of wires consists of a number of wire segments equal to two times a number of vertices of the axial cross section.

Example 8: The occluder device of any example herein, in particular examples 1-7, wherein the core form includes two opposing forms that converge at a neck portion and expand in diameter moving away from the neck portion.

Example 9: The occluder device of any example herein, in particular example 8, wherein each of the opposing forms is a truncated pyramid.

Example 10: The occluder device of any example herein, in particular example 9, wherein the opposing forms have six lateral faces.

Example 11: The occluder device of any example herein, in particular examples 8-10, wherein each of the opposing forms is a frustoconical form.

Example 12: The occluder device of any example herein, in particular examples 1-11, wherein the first covering is configured to fold along each of the first plurality of wires to form first transverse pleats that, in a partially-expanded configuration of the first covering, radiate from an axis of the core form and circumferentially curve about the axis of the core form, and the second covering is configured to fold along each of the second plurality of wires to form transverse pleats that, in a partially-expanded configuration of the second covering, radiate from the axis of the core form and circumferentially curve about the axis of the core form.

Example 13: The occluder device of any example herein, in particular example 12, wherein, in a fully compressed configuration each of the first covering and the second covering forms an open cylinder, and the first and second coverings are each open axially away from a neck region of the core form.

Example 14: The occluder device of any example herein, in particular example 12 or 13, wherein, in the partially-expanded configuration, the first covering has an axially concave form.

Example 15. A defect cover comprising a first set of wires emanating radially from a central portion of the defect cover, a second set of wires emanating radially from the central portion, the second set of wires being interleaved with the first set of wires, and a covering disposed against the first set of wires and the second set of wires and configured to fold about each of the first set of wires and the second set of wires to form folds configured to wrap around the central portion of the defect cover to assume a compressed configuration of the defect cover.

Example 16: The defect cover of any example herein, in particular example 15, wherein the defect cover is configured to assume an expanded configuration in which the covering is substantially fat.

Example 17: The defect cover of any example herein, in particular example 16, wherein, when the defect cover is in the expanded configuration, the first and second sets of wires are circumferentially curved.

Example 18: The defect cover of any example herein, in particular examples 15-17, wherein, when the defect cover is in the compressed configuration the first set of wires is wrapped circumferentially around an axis of the defect cover at a first angle with respect to an axial plane associated with the defect cover, and the second set of wires is wrapped circumferentially around the axis of the defect cover at a second angle with respect to the axial plane, the second angle being greater than the first angle.

Example 19: The defect cover of any example herein, in particular example 18, wherein, when the defect cover is in the compressed configuration, the first set of wires lie in the axial plane.

Example 20: The defect cover of any example herein, in particular examples 15-19, wherein the central portion is associated with a polygonal core.

Example 21: The defect cover of any example herein, in particular example 20, wherein the first set of wires runs alongside sides of the polygonal core, and the second set of wires emanates away from respective vertices of the polygonal core.

Example 22: The defect cover of any example herein, in particular example 20 or 22, wherein each vertex of the polygonal core has one wire of the first set of wires and one wire of the second set of wires emanating therefrom.

Example 23: The defect cover of any example herein, in particular examples 15-22, wherein the folds comprise alternating crests and troughs, the first set of wires is associated with the troughs, and the second set of wires is associated with the crests.

Example 24. A method of delivering an occluder device, the method comprising providing an occluder device comprising, a core form having first and second axial ends, a first cover including a first plurality of wires emanating radially from the first axial end of the core form and a first covering coupled to one or more of the first plurality of wires, and a second cover including a second plurality of wires emanating from the second axial end of the core form and a second covering coupled to one or more of the second plurality of wires. The method further comprises wrapping the first plurality of wires around the first axial end of the core form to compress the first cover, wrapping the second plurality of wires around the second axial end of the core form to compress the second cover, disposing the occluder device in a delivery system, advancing the delivery system through a defect in a tissue wall, deploying the first cover from the delivery system on a distal side of the tissue wall to cause a perimeter of the first cover to expand radially outward and toward the tissue wall, deploying the core form from the delivery system at least partially within the defect in the tissue wall, and deploying the second cover from the delivery system on a proximal side of the tissue wall to cause a perimeter of the second cover to expand radially outward and toward the tissue wall.

Example 25: The method of any example herein, in particular example 24, wherein said deploying the second cover involves causing the second cover to partially expand to form an inwardly-convex form.

Example 26: The method of any example herein, in particular example 25, wherein the inwardly-convex form is configured to seat in a concave portion of the tissue wall.

Depending on the example, certain acts, events, or functions of any of the processes or algorithms described herein can be performed in a different sequence, may be added, merged, or left out altogether. Thus, in certain examples, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain examples require at least one of X, at least one of Y and at least one of Z to each be present.

It should be appreciated that in the above description of examples, various features are sometimes grouped together in a single example. Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular example herein can be applied to or used with any other example(s). Further, no component, feature, step, or group of components, features, or steps are necessary or indispensable for each example. Thus, it is intended that the scope of the inventions herein disclosed and claimed below should not be limited by the particular examples described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example examples belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. An occluder device comprising:

a core form having first and second axial ends;

a first plurality of wires emanating radially from the first axial end of the core form, the first plurality of wires being configured to circumferentially wrap around an axis of the core form, wherein the first plurality of wires includes a plurality of pairs of wires, with each of the plurality of pairs of wires originating from a respective vertex of a polygonal profile of the first axial end of the core form and being deflected circumferentially relative to a tangential direction at the respective vertex;

a first covering coupled to at least one of the first plurality of wires or the first axial end of the core form, the first covering being folded at each of the first plurality of wires to form a plurality of radial pleats including alternating peak and valley pleats that in a compressed delivery configuration, are wrapped circumferentially around a body of the core form;

a second plurality of wires emanating radially from the second axial end of the core form, the second plurality of wires being configured to circumferentially wrap around the axis of the core form; and a second covering coupled to at least one of the second plurality of wires or the second axial end of the core form.

2. The occluder device of claim 1, wherein:

the first plurality of wires includes first and second alternating sets of wires;

the first set of wires is configured to wrap circumferentially around the axis of the core form at a first angle with respect to an axial plane associated with the core form; and the second set of wires is interleaved with the first set of wires and configured to wrap circumferentially around the axis of the core form at a second angle with respect to the axial plane, the second angle being greater than the first angle.

3. The occluder device of claim 2, wherein the first set of wires is disposed on a first side of the first covering, and the second set of wires is disposed on a second side of the first covering that is opposite the first side.

4. The occluder device of claim 1, wherein the core form has a polygonal axial cross section at a central waist of the core form.

5. The occluder device of claim 4, wherein the core form has a hexagonal axial cross section at the first axial end.

6. The occluder device of claim 4, wherein the first plurality of wires consists of a number of wire segments equal to two times a number of vertices of the polygonal axial cross section.

7. The occluder device of claim 1, wherein the core form includes two opposing forms that converge at a central waist portion and expand in diameter moving away from the central waist portion.

8. The occluder device of claim 7, wherein each of the two opposing forms is a truncated pyramid.

9. The occluder device of claim 8, wherein the two opposing forms have six lateral faces.

10. The occluder device of claim 7, wherein each of the two opposing forms has a frustoconical form.

11. The occluder device of claim 1, wherein:

the second covering is configured to fold along each of the second plurality of wires to form transverse pleats that, in a partially-expanded configuration of the second covering, radiate from the axis of the core form and circumferentially curve about the axis of the core form.

12. The occluder device of claim 11, wherein, in a fully compressed configuration, each of the first covering and the second covering forms an open cylinder, and the first and second coverings are each open axially away from a neck region of the core form.

13. The occluder device of claim 11, wherein, in the partially-expanded configuration, the second covering has an axially concave form.

14. A defect cover comprising:

a first set of wires emanating radially from a central portion of the defect cover;

a second set of wires emanating radially from the central portion, the second set of wires being interleaved with the first set of wires; and a covering disposed against the first set of wires and the second set of wires and configured to fold about each of the first set of wires and the second set of wires to form folds configured to wrap around the central portion of the defect cover to assume a compressed configuration of the defect cover;

wherein:

the folds form a plurality of radial pleats that include alternating peak folds pleats corresponding to the first set of wires and valley folds pleats corresponding to the second set of wires, the alternating peak pleats and valley pleats being wrapped circumferentially around an axis of the central portion in the compressed configuration;

the first set of wires and the peak folds pleats are adapted to wrap circumferentially around the central portion of the defect cover such that the first set of wires are wrapped at a first angle greater than 30° with respect to an axial plane of the defect cover; and the second set of wires and the valley folds pleats are adapted to wrap circumferentially around the central portion of the defect cover such that the second set of wires are wrapped at a second angle within 15° of the axial plane.

15. The defect cover of claim 14, wherein the defect cover is configured to assume an expanded configuration in which the covering is substantially flat.

16. The defect cover of claim 15, wherein, when the defect cover is in the expanded configuration, the first and second sets of wires are circumferentially curved.

17. An occluder device comprising:

a core form having first and second axial ends;

a first plurality of wires emanating radially from the first axial end of the core form, the first plurality of wires being configured to circumferentially wrap around an axis of the core form;

a first covering coupled to at least one of the first plurality of wires or the first axial end of the core form;

a second plurality of wires emanating radially from the second axial end of the core form, the second plurality of wires being configured to circumferentially wrap around the axis of the core form; and a second covering coupled to at least one of the second plurality of wires or the second axial end of the core form;

wherein:

in a compressed delivery configuration, the first covering is folded at each of the first plurality of wires forming a plurality of radial pleats including alternating peak and valley pleats that are wrapped circumferentially around a body of the core form; and in an expanded deployed configuration, the first plurality of wires extend radially outwardly with the first covering expanded in an unfolded configuration.

18. The occluder device of claim 17, wherein the first plurality of wires includes a plurality of pairs of wires, with each of the plurality of pairs of wires including first and second wires emanating from a common point associated with the first axial end of the core form.

19. The occluder device of claim 17, wherein, in the compressed delivery configuration:

the peak pleats are at a first angle greater than 30° with respect to an axial plane of the occluder device; and the valley pleats are wrapped at a second angle within 15° of the axial plane.

* * * * *